US008263102B2

(12) United States Patent
Labrecque et al.

(10) Patent No.: US 8,263,102 B2
(45) Date of Patent: *Sep. 11, 2012

(54) DRUG DELIVERY COATING FOR USE WITH A STENT

(75) Inventors: Roger Labrecque, Londonderry, NH (US); Geoffrey Moodie, Hudson, NH (US); Joseph Ferraro, Londonderry, NH (US); Lisa Rogers, Londonderry, NH (US); Paul Martakos, Pelham, NH (US); Theodore Karwoski, Hollis, NH (US); Steve A. Herweck, Nashua, NH (US)

(73) Assignee: Atrium Medical Corporation, Hudson, NH (US)

( * ) Notice: Subject to any disclaimer, the term of this patent is extended or adjusted under 35 U.S.C. 154(b) by 1264 days.

This patent is subject to a terminal disclaimer.

(21) Appl. No.: 11/236,908

(22) Filed: Sep. 28, 2005

(65) Prior Publication Data
US 2006/0067974 A1 Mar. 30, 2006

Related U.S. Application Data

(60) Provisional application No. 60/613,745, filed on Sep. 28, 2004.

(51) Int. Cl.
A61F 2/00 (2006.01)
A61K 9/00 (2006.01)

(52) U.S. Cl. ......... 424/423; 424/484; 424/425; 424/426
(58) Field of Classification Search .................. None
See application file for complete search history.

(56) References Cited

U.S. PATENT DOCUMENTS

| 2,368,306 | A | 1/1945 | Kiefer et al. |
| 2,986,540 | A | 5/1961 | Posnansky |
| 3,464,413 | A | 9/1969 | Goldfarb et al. |
| 3,556,294 | A | 1/1971 | Walck et al. |
| 3,567,820 | A | 3/1971 | Sperti |
| 3,967,728 | A | 7/1976 | Gordon et al. |
| 4,308,120 | A | 12/1981 | Pennewiss et al. |
| 4,323,547 | A | 4/1982 | Knust et al. |
| 4,557,925 | A | 12/1985 | Lindahl et al. |
| 4,664,114 | A | 5/1987 | Ghodstain |
| 4,813,210 | A | 3/1989 | Masuda et al. |
| 4,814,329 | A | 3/1989 | Harsanyi et al. |
| 4,847,301 | A | 7/1989 | Murray |
| 4,880,455 | A | 11/1989 | Blank |
| 4,883,667 | A | 11/1989 | Eckenhoff |
| 4,886,787 | A | 12/1989 | De Belder et al. |
| 4,894,231 | A | 1/1990 | Moreau et al. |
| 4,895,724 | A | 1/1990 | Cardinal et al. |
| 4,911,707 | A | 3/1990 | Heiber et al. |
| 4,941,308 | A | 7/1990 | Grabenkort et al. |
| 4,952,419 | A | 8/1990 | De Leon et al. |
| 4,968,302 | A | 11/1990 | Schluter et al. |
| 5,017,229 | A | 5/1991 | Burns et al. |
| 5,132,115 | A | 7/1992 | Wolter et al. |
| 5,147,374 | A | 9/1992 | Fernandez |
| 5,151,272 | A | 9/1992 | Engstrom et al. |
| 5,171,148 | A | 12/1992 | Wasserman et al. |
| 5,176,956 | A | 1/1993 | Jevne et al. |
| 5,179,174 | A | 1/1993 | Elton |
| 5,254,105 | A | 10/1993 | Haaga |
| 5,356,432 | A | 10/1994 | Rutkow et al. |
| 5,368,602 | A | 11/1994 | de la Torre |
| 5,371,109 | A | 12/1994 | Engstrom et al. |
| 5,380,328 | A | 1/1995 | Morgan |
| 5,387,658 | A * | 2/1995 | Schroder et al. ............... 525/530 |
| 5,403,283 | A | 4/1995 | Luther |
| 5,447,940 | A | 9/1995 | Harvey et al. |
| 5,464,650 | A | 11/1995 | Berg et al. |
| 5,480,653 | A | 1/1996 | Aguadisch et al. |
| 5,509,899 | A | 4/1996 | Fan et al. |
| 5,579,149 | A | 11/1996 | Moret et al. |
| 5,580,923 | A | 12/1996 | Yeung et al. |
| 5,591,230 | A | 1/1997 | Horn et al. |
| 5,593,441 | A | 1/1997 | Lichtenstein et al. |
| 5,612,074 | A * | 3/1997 | Leach ............................ 426/74 |
| 5,614,284 | A | 3/1997 | Kranzler et al. |
| 5,627,077 | A | 5/1997 | Dyllick-Brenzinger et al. |
| 5,637,113 | A | 6/1997 | Tartaglia et al. |
| 5,665,115 | A | 9/1997 | Cragg |
| 5,695,525 | A | 12/1997 | Mulhauser et al. |

(Continued)

FOREIGN PATENT DOCUMENTS

EP 0 471 566 2/1992

(Continued)

OTHER PUBLICATIONS

Cure in Academic Press Dictionary of Science and Technology 1992.*
EM, "Coating Types and Characteristics", pp. 4-1 to 4-24, Apr. 30, 1995.*
Wikipedia, Sirolimus, pp. 1-13, date accessed May 11, 2011.*
A paper entitled, "Evaluation of the Biocompatibility and Drug Delivery Capabilities of Biological Oil Based Stent Coatings," by Li, Shengqiao of the Katholieke Universiteit Leuven.
"Polymerization" Merriam-Webster Online Dictionary, retrieved from <www.merriam-webster.com> on Dec. 13, 2009; Merriam-Webster's Inc. 2009; pp. 1.
Ahuja, et al. Journal of Indian Pediatric Surgery 2002 7:15-20.
Autosuture, "ParietexTM Composite OS Series Mesh," retrieved online at http://www.autosuture.com/AutoSuture/pagebuilder.aspx?topicID=135734&breadcrumbs=135601:0 (2007).
Binder et al., "Chromatographic Analysis of Seed Oils. Fatty Acid Composition of Castor Oil," The Journal of the American Oil Chemists' Society, vol. 39:513-517 (1962).

(Continued)

Primary Examiner — Scott Long
Assistant Examiner — Lyndsey Beckhardt
(74) Attorney, Agent, or Firm — Morse, Barnes-Brown & Pendleton, P.C.; Sean D. Detweiler, Esq.

(57) ABSTRACT

A coated medical device an a method of providing a coating on an implantable medical device result in a medical device having a bio-absorbable coating. The coating includes a bio-absorbable carrier component. In addition to the bio-absorbable carrier component, a therapeutic agent component can also be provided. The coated medical device is implantable in a patient to effect controlled delivery of the coating, including the therapeutic agent, to the patient.

56 Claims, 7 Drawing Sheets

U.S. PATENT DOCUMENTS

| | | | |
|---|---|---|---|
| 5,700,286 A | 12/1997 | Tartaglia et al. | |
| 5,736,152 A | 4/1998 | Dunn | |
| 5,753,259 A | 5/1998 | Engstrom et al. | |
| 5,760,081 A | 6/1998 | Leaf et al. | |
| 5,766,246 A | 6/1998 | Mulhauser et al. | |
| 5,766,710 A | 6/1998 | Turnlund et al. | |
| 5,817,343 A | 10/1998 | Burke | |
| 5,824,082 A | 10/1998 | Brown | |
| 5,837,313 A * | 11/1998 | Ding et al. | 427/2.21 |
| 5,843,919 A | 12/1998 | Burger | |
| 5,874,470 A | 2/1999 | Nehne et al. | |
| 5,879,359 A | 3/1999 | Dorigatti et al. | |
| 5,898,040 A | 4/1999 | Shalaby et al. | |
| 5,906,831 A | 5/1999 | Larsson et al. | |
| 5,931,165 A | 8/1999 | Reich et al. | |
| 5,955,502 A | 9/1999 | Hansen et al. | |
| 5,986,043 A | 11/1999 | Hubbell et al. | |
| 6,005,004 A | 12/1999 | Katz et al. | |
| 6,010,766 A * | 1/2000 | Braun et al. | 428/182 |
| 6,010,776 A * | 1/2000 | Exsted et al. | 428/305.5 |
| 6,015,844 A | 1/2000 | Harvey et al. | |
| 6,028,164 A | 2/2000 | Loomis | |
| 6,040,330 A * | 3/2000 | Hausheer et al. | 514/408 |
| 6,056,970 A | 5/2000 | Greenwalt et al. | |
| 6,077,698 A | 6/2000 | Swan et al. | |
| 6,083,950 A | 7/2000 | Anand et al. | |
| 6,090,809 A | 7/2000 | Anand et al. | |
| 6,093,792 A | 7/2000 | Gross et al. | |
| 6,117,911 A | 9/2000 | Grainger et al. | |
| 6,120,539 A | 9/2000 | Eldridge et al. | |
| 6,120,789 A | 9/2000 | Dunn | |
| 6,132,765 A | 10/2000 | DiCosmo et al. | |
| 6,146,358 A | 11/2000 | Rowe | |
| 6,152,944 A | 11/2000 | Holman et al. | |
| 6,176,863 B1 | 1/2001 | Kugel et al. | |
| 6,193,746 B1 | 2/2001 | Strecker | |
| 6,197,357 B1 | 3/2001 | Lawton et al. | |
| 6,203,551 B1 | 3/2001 | Wu | |
| 6,206,916 B1 | 3/2001 | Furst | |
| 6,211,315 B1 | 4/2001 | Larock et al. | |
| 6,228,383 B1 | 5/2001 | Hansen et al. | |
| 6,229,032 B1 | 5/2001 | Jacobs et al. | |
| 6,245,811 B1 | 6/2001 | Horrobin et al. | |
| 6,254,634 B1 | 7/2001 | Anderson et al. | |
| 6,262,109 B1 | 7/2001 | Clark et al. | |
| 6,273,913 B1 | 8/2001 | Wright et al. | |
| 6,284,268 B1 | 9/2001 | Mishra et al. | |
| 6,299,604 B1 | 10/2001 | Ragheb et al. | |
| 6,326,360 B1 * | 12/2001 | Kanazawa et al. | 514/53 |
| 6,331,568 B1 | 12/2001 | Horrobin | |
| 6,346,110 B2 | 2/2002 | Wu | |
| 6,358,556 B1 | 3/2002 | Ding et al. | |
| 6,364,893 B1 | 4/2002 | Sahatjian et al. | |
| 6,368,658 B1 | 4/2002 | Schwarz et al. | |
| 6,369,039 B1 | 4/2002 | Palasis et al. | |
| 6,387,379 B1 | 5/2002 | Goldberg et al. | |
| 6,410,587 B1 | 6/2002 | Grainger et al. | |
| 6,444,318 B1 | 9/2002 | Guire et al. | |
| 6,451,373 B1 | 9/2002 | Hossainy et al. | |
| 6,465,525 B1 | 10/2002 | Guire et al. | |
| 6,471,980 B2 | 10/2002 | Sirhan et al. | |
| 6,479,683 B1 | 11/2002 | Abney et al. | |
| 6,491,938 B2 | 12/2002 | Kunz | |
| 6,500,453 B2 | 12/2002 | Brey et al. | |
| 6,503,556 B2 * | 1/2003 | Harish et al. | 427/2.24 |
| 6,525,145 B2 | 2/2003 | Gevaert et al. | |
| 6,527,801 B1 | 3/2003 | Dutta | |
| 6,534,693 B2 | 3/2003 | Fischell et al. | |
| 6,548,081 B2 | 4/2003 | Sadozai et al. | |
| 6,565,659 B1 | 5/2003 | Pacetti et al. | |
| 6,569,441 B2 | 5/2003 | Kunz et al. | |
| 6,599,323 B2 | 7/2003 | Melican et al. | |
| 6,610,035 B2 | 8/2003 | Yang et al. | |
| 6,610,068 B1 | 8/2003 | Yang et al. | |
| 6,630,151 B1 | 10/2003 | Tarletsky et al. | |
| 6,630,167 B2 | 10/2003 | Zhang | |
| 6,632,822 B1 | 10/2003 | Rickards et al. | |
| 6,641,611 B2 | 11/2003 | Jayaraman | |
| 6,645,547 B1 | 11/2003 | Shekalim | |
| 6,663,880 B1 | 12/2003 | Roorda et al. | |
| 6,669,735 B1 | 12/2003 | Pelissier | |
| 6,670,355 B2 | 12/2003 | Azrolan et al. | |
| 6,677,342 B2 | 1/2004 | Wolff et al. | |
| 6,677,386 B1 | 1/2004 | Giezen et al. | |
| 6,685,956 B2 | 2/2004 | Chu et al. | |
| 6,730,064 B2 | 5/2004 | Ragheb et al. | |
| 6,753,071 B1 | 6/2004 | Pacetti | |
| 6,761,903 B2 | 7/2004 | Chen et al. | |
| 6,764,509 B2 | 7/2004 | Chinn et al. | |
| 6,776,796 B2 | 8/2004 | Falotico et al. | |
| 6,794,485 B2 | 9/2004 | Shalaby et al. | |
| 6,833,004 B2 | 12/2004 | Ishii et al. | |
| 6,852,330 B2 | 2/2005 | Bowman et al. | |
| 6,875,230 B1 | 4/2005 | Morita et al. | |
| 6,884,428 B2 | 4/2005 | Binette et al. | |
| 6,887,270 B2 | 5/2005 | Miller et al. | |
| 6,899,729 B1 | 5/2005 | Cox et al. | |
| 6,918,927 B2 | 7/2005 | Bates et al. | |
| 6,996,952 B2 | 2/2006 | Gupta et al. | |
| 7,070,858 B2 | 7/2006 | Shalaby et al. | |
| 7,101,381 B2 | 9/2006 | Ford et al. | |
| 7,152,611 B2 | 12/2006 | Brown et al. | |
| 7,323,189 B2 * | 1/2008 | Pathak | 424/423 |
| 7,415,811 B2 | 8/2008 | Gottlieb et al. | |
| 8,124,127 B2 | 2/2012 | Faucher et al. | |
| 2001/0025196 A1 | 9/2001 | Chinn et al. | |
| 2001/0051595 A1 | 12/2001 | Lyons et al. | |
| 2002/0002154 A1 | 1/2002 | Guivarc'h et al. | |
| 2002/0007209 A1 | 1/2002 | Scheerder et al. | |
| 2002/0012741 A1 | 1/2002 | Heinz et al. | |
| 2002/0026899 A1 | 3/2002 | McLaughlin et al. | |
| 2002/0026900 A1 | 3/2002 | Huang et al. | |
| 2002/0032414 A1 | 3/2002 | Ragheb et al. | |
| 2002/0098278 A1 | 7/2002 | Bates et al. | |
| 2002/0116045 A1 | 8/2002 | Eidenschink | |
| 2002/0120333 A1 | 8/2002 | Keogh et al. | |
| 2002/0122877 A1 | 9/2002 | Harish et al. | |
| 2002/0142089 A1 | 10/2002 | Koike et al. | |
| 2002/0193829 A1 | 12/2002 | Kennedy et al. | |
| 2003/0003125 A1 | 1/2003 | Nathan et al. | |
| 2003/0004564 A1 | 1/2003 | Elkins et al. | |
| 2003/0055403 A1 | 3/2003 | Nestenborg et al. | |
| 2003/0065292 A1 | 4/2003 | Darouiche et al. | |
| 2003/0065345 A1 | 4/2003 | Weadock | |
| 2003/0069632 A1 | 4/2003 | De Scheerder et al. | |
| 2003/0072784 A1 | 4/2003 | Williams | |
| 2003/0077272 A1 | 4/2003 | Pathak | |
| 2003/0077310 A1 | 4/2003 | Pathak et al. | |
| 2003/0077452 A1 | 4/2003 | Guire et al. | |
| 2003/0083740 A1 * | 5/2003 | Pathak | 623/1.43 |
| 2003/0086958 A1 | 5/2003 | Arnold et al. | |
| 2003/0094728 A1 | 5/2003 | Tayebi | |
| 2003/0130206 A1 | 7/2003 | Koziak et al. | |
| 2003/0152609 A1 | 8/2003 | Fischell et al. | |
| 2003/0175408 A1 | 9/2003 | Timm et al. | |
| 2003/0176915 A1 | 9/2003 | Wright et al. | |
| 2003/0181975 A1 | 9/2003 | Ishii et al. | |
| 2003/0191179 A1 | 10/2003 | Joshi-Hangal et al. | |
| 2003/0204168 A1 | 10/2003 | Bosma et al. | |
| 2003/0204618 A1 | 10/2003 | Foster et al. | |
| 2003/0207019 A1 | 11/2003 | Shekalim et al. | |
| 2003/0220297 A1 | 11/2003 | Berstein et al. | |
| 2004/0006296 A1 | 1/2004 | Fischell et al. | |
| 2004/0014810 A1 | 1/2004 | Horrobin | |
| 2004/0018228 A1 | 1/2004 | Fischell et al. | |
| 2004/0039441 A1 | 2/2004 | Rowland et al. | |
| 2004/0071756 A1 | 4/2004 | Fischell et al. | |
| 2004/0072849 A1 | 4/2004 | Schreiber et al. | |
| 2004/0073284 A1 | 4/2004 | Bates et al. | |
| 2004/0133275 A1 | 7/2004 | Mansmann | |
| 2004/0137066 A1 | 7/2004 | Jayaraman | |
| 2004/0137179 A1 | 7/2004 | Matsuda et al. | |
| 2004/0142094 A1 | 7/2004 | Narayanan | |
| 2004/0146546 A1 * | 7/2004 | Gravett et al. | 424/445 |
| 2004/0156879 A1 | 8/2004 | Muratoglu et al. | |
| 2004/0161464 A1 | 8/2004 | Domb | |
| 2004/0167572 A1 | 8/2004 | Roth et al. | |

| | | |
|---|---|---|
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0058881 A1 | 3/2006 | Trieu |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0202149 A1 | 8/2007 | Faucher et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0206305 A1 | 8/2008 | Herweck et al. |
| 2008/0279929 A1 | 11/2008 | Devane et al. |
| 2009/0011116 A1 | 1/2009 | Herweck et al. |
| 2009/0047414 A1 | 2/2009 | Corbeil et al. |
| 2009/0181937 A1 | 7/2009 | Faucher et al. |
| 2009/0208552 A1 | 8/2009 | Faucher et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |

FOREIGN PATENT DOCUMENTS

| | | |
|---|---|---|
| EP | 0610731 | 8/1994 |
| EP | 0623354 B1 | 11/1994 |
| EP | 0730864 B1 | 9/1996 |
| EP | 0790822 B1 | 8/1997 |
| EP | 0873133 B1 | 10/1998 |
| EP | 0917561 B1 | 5/1999 |
| EP | 1140243 B1 | 10/2001 |
| EP | 1181943 A1 | 2/2002 |
| EP | 1270024 A1 | 1/2003 |
| EP | 1273314 A1 | 1/2003 |
| EP | 1364628 A1 | 11/2003 |
| EP | 1520795 | 4/2005 |
| EP | 1557183 A1 | 7/2005 |
| EP | 1 402 906 | 6/2011 |
| WO | WO 86/00912 | 2/1986 |
| WO | WO-90/01969 A1 | 3/1990 |
| WO | WO-95/26715 A2 | 10/1995 |
| WO | WO-97/02042 A1 | 1/1997 |
| WO | WO-97/09367 A1 | 3/1997 |
| WO | WO-97/13528 A1 | 4/1997 |
| WO | WO-98/30206 A1 | 7/1998 |
| WO | WO-98/54275 A3 | 12/1998 |
| WO | WO 99/25336 | 5/1999 |
| WO | WO-00/40278 A1 | 7/2000 |
| WO | WO-00/62830 A2 | 10/2000 |
| WO | WO-01/24866 A1 | 4/2001 |
| WO | WO-01/26585 A1 | 4/2001 |
| WO | WO 01/37808 | 5/2001 |
| WO | WO 01/60586 | 8/2001 |
| WO | WO-01/66036 A2 | 9/2001 |
| WO | WO-01/76649 A1 | 10/2001 |
| WO | WO-02/49535 A2 | 6/2002 |
| WO | WO-02/100455 A2 | 12/2002 |
| WO | WO-03/000308 A1 | 1/2003 |
| WO | WO-03/015748 A2 | 2/2003 |
| WO | WO-03/028622 A2 | 4/2003 |
| WO | WO-03/037397 A2 | 5/2003 |
| WO | WO-03/037398 A2 | 5/2003 |
| WO | WO 03/039612 * | 5/2003 |
| WO | WO-03/039612 A1 | 5/2003 |
| WO | WO-03/041756 A1 | 5/2003 |
| WO | WO-03/070125 A1 | 8/2003 |
| WO | WO-03/092741 A1 | 11/2003 |
| WO | WO 03/092779 | 11/2003 |
| WO | WO-2004/004598 A2 | 1/2004 |
| WO | WO-2004/006976 A1 | 1/2004 |
| WO | WO-2004/006978 A1 | 1/2004 |
| WO | WO 2004/028583 | 4/2004 |
| WO | WO 2004/091684 | 10/2004 |
| WO | WO-2005/000165 A1 | 1/2005 |
| WO | WO-2005/016400 A1 | 2/2005 |
| WO | WO-2005/053767 A1 | 6/2005 |
| WO | WO 2005/073091 | 8/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | WO 2008/057328 | 5/2008 |

OTHER PUBLICATIONS

De Scheerder, Ivan K., et al. "Biocompatibility of polymer-coated oversized metallic stents implanted in normal porcine coronary arteries," Atherosclerosis, vol. 114:105-114, 1995.

Guler, et al. "Some empirical equations for oxopolymerization of linseed oil," Progress in Organic Coatings, vol. 51:365-371 (2004).

Jonasson, Lena, et al., "Cyclosporon A inhibits smooth muscle proliferation in the vascular response to injury," Proc. Natl. Acad. Sci. USA, vol. 85: 2303-2306 (1988).

Mallegol, et al., "Drier Influence on the Curing of Linseed Oil," Progress in Organic Coatings 39:107-113 (2000).

Morse, Richard "Molecular Distillation of Polymerized Drying Oils," Industrial and Engineering Chemisry 33:1039-1043 (1941).

Ogunniyi, D.S., "Castor oil: A vital industrial raw material," Biosource Technology, vol. 97: 1086-1091 (2006).

Redman, L.V., et al., "The drying rate of raw paint oils—a comparison," The Journal of Industrial and Engineering Chemistry, vol. 5: 630-636 (1913).

Rutkow, Ira M., et al., "'Tension-free' inguinal herniorrhaphy: A preliminary report on the 'mesh plug' technique," Surgery, vol. 114:3-8 (1993).

Shahidi, Fereidoon ed.; "Bailey's Industrial Oil and Fats Products" 2005; John Wiley and Sons; vol. 5, Edible Oil and Fat Products: Processing Technologies, pp. 1-15.

Van der Giessen, et al, "Marked Inflammatory Sequelae to Implantation of Biodegradable and Nonbiodegradable Polymers in Porcine Coronary Arteries," Circulation, 1996, 94:1690-1697.
Websters Dictionary Online, Accessed on Feb. 13, 2009, entry for "polymer" p. 1 of 1.
Timir-Balizsy et al., "Chemical Principals of Textile Conservation," Oxford: Elsevier Science Ltd., 1998:117-119.
Crivello et al., "Epoxidized triglycerides as renewable monomers in photoinitiated cationic polymerization," Chem. Mater, 1992:692-699.
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US05/034941, dated May 4, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Supplementary European Search Report in Application No. EP 05 80 4291, dated Jul. 26, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 85 8430, dated Aug. 18, 2011.
Final Office Action for U.S. Appl. No. 11/236,943, mailed Dec. 23, 2009.
Non-Final Office Action for U.S. Appl. No. 11/236,943, mailed Mar. 5, 2009.
Non-final Office Action for U.S. Appl. No. 11/236,977, mailed Aug. 3, 2009.
Final Office Action for U.S. Appl. No. 11/237,263, mailed Jul. 7, 2010.
Non-final Office Action for U.S. Appl. No. 11/237,263, mailed Oct. 7, 2009.
Final Office Action for U.S. Appl. No. 11/237,264, mailed Jun. 2, 2010.
Non-final Office Action for U.S. Appl. No. 11/237,264, mailed Oct. 5, 2009.
Final Office Action for U.S. Appl. No. 11/701,799, mailed Nov. 23, 2010.
Non-Final Office Action for U.S. Appl. No. 11/701,799, mailed Aug. 17, 2011.
Non-final Office Action for U.S. Appl. No. 11/237,420, mailed Mar. 5, 2009.
Final Office Action for U.S. Appl. No. 11/237,420, mailed Nov. 4, 2009.
Non-final Office Action for U.S. Appl. No. 11/237,420, mailed Dec. 6, 2010.
Final Office Action for U.S. Appl. No. 11/237,420, mailed Jul. 13, 2011.
Non-final Office Action for U.S. Appl. No. 11/238,532, mailed Mar. 30, 2009.
Final Office Action for U.S. Appl. No. 11/238,532, mailed Sep. 9, 2009.
Final Office Action for U.S. Appl. No. 11/238,554, mailed May 12, 2010.
Non-final Office Action for U.S. Appl. No. 11/238,554, mailed Oct. 9, 2009.
Final Office Action for U.S. Appl. No. 11/238,554, mailed May 1, 2009.
Non-final Office Action for U.S. Appl. No. 11/238,554, mailed Jul. 25, 2008.
Non-final Office Action for U.S. Appl. No. 11/238,564, mailed Apr. 16, 2008.
Final Office Action for U.S. Appl. No. 11/238,564, mailed Aug. 6, 2009.
Non-final Office Action for U.S. Appl. No. 11/239,555, mailed Mar. 30, 2009.
Non-final Office Action for U.S. Appl. No. 11/525,328, mailed Apr. 30, 2007.
Non-final Office Action for U.S. Appl. No. 11/525,390, mailed Jul. 14, 2010.
Final Office Action for U.S. Appl. No. 11/525,390, mailed Feb. 21, 2011.
Non-final Office Action for U.S. Appl. No. 11/525,390, mailed Jul. 11, 2011.
Final Office Action for U.S. Appl. No. 11/582,135, mailed May 12, 2011.
Non-final Office Action for U.S. Appl. No. 11/582,135, mailed Nov. 9, 2010.
Non-final Office Action for U.S. Appl. No. 11/582,135, mailed Jan. 6, 2010.
Non-final Office Action for U.S. Appl. No. 11/582,135, mailed May 12, 2009.
Non-final Office Action for U.S. Appl. No. 11/701,799, mailed Apr. 12, 2010.
Non-final Office Action for U.S. Appl. No. 11/978,840, mailed Dec. 3, 2010.
Non-final Office Action for U.S. Appl. No. 11/980,155, mailed Mar. 24, 2011.
Non-final Office Action for U.S. Appl. No. 12/075,223, mailed Dec. 8, 2010.
Non-final Office Action for U.S. Appl. No. 12/075,223, mailed Aug. 11, 2011.
Non-final Office Action for U.S. Appl. No. 12/325,546, mailed Feb. 25, 2010.
Final Office Action for U.S. Appl. No. 12/325,546, mailed Aug. 31, 2010.
Non-final Office Action for U.S. Appl. No. 12/364,763, mailed Dec. 11, 2009.
Final Office Action for U.S. Appl. No. 12/364,763, mailed Sep. 21, 2010.

Interview summary for U.S. Appl. No. 11/237,420 mailed May 5, 2009.
Interview summary for U.S. Appl. No. 11/582,135 mailed Dec. 7, 2010.
Interview summary for U.S. Appl. No. 12/325,546 mailed Dec. 2, 2010.
Interview summary for U.S. Appl. No. 12/364,763 mailed Dec. 2, 2010.
Encyclopedia Britannica Online, "Surface Coating," available online at http://www.britannica.com/EBchecked/topic/575029/surface-coating>, date accessed Jun. 17, 2011.
Final Office Action for U.S. Appl. No. 11/978,840, mailed Jun. 22, 2011.
Non-Final Office Action for U.S. Appl. No. 11/582,135, mailed Oct. 14, 2011.
Camurus, "In our endeavors to create the unique, we start with the best. Your product."
Drummond, Calum J. et al, "Surfactant self-assembly objects as novel drug delivery vehicles," *Current Opinion in Colloid & Interface Science*, vol. 4:449-456 (2000).
Engström, Sven, "Drug Delivery from Cubic and Other Lipid-water Phases," *Lipid Technology*, vol. 2(2):42-45 (1990).
Hwang, Chao-Wei et al, "Physiological Transport Forces Govern Drug Distribution for Stent-Based Delivery," *Circulation*, vol. 104:600-605 (2001).
Oberhoff, Martin et al, "Local and Systemic Delivery of Low Molecular Weight Heparin Following PTCA: Acute Results and 6-Month Follow-Up of the Initial Clinical Experience With the Porous Balloon (PILOT-Study)," *Catheterization and Cardiovascular Diagnosis*, vol. 44:267-274 (1998).
Salu, Koen J. et al, "Addition of cytochalasin D to a biocompatible oil stent coating inhibits intimal hyperplasia in a porcine coronary model," *Coronary Artery Disease*, vol. 14(8):545-555 (2003).
Scheller, Bruno et al, "Addition of Paclitaxel to Contrast Media Prevents Restenosis After Coronary Stent Implantation," *Journal of the American College of Cardiology*, vol. 42(8):1415-1420 (2003).
Final Office Action for U.S. Appl. No. 11/980,155, mailed Oct. 21, 2011.
Non-Final Office Action for U.S. Appl. No. 12/182,261, mailed Dec. 21, 2011.
Non-Final Office Action for U.S. Appl. No. 12/401,243, mailed Jan. 5, 2012.
Notice of Allowance for U.S. Appl. No. 11/582,135, mailed Jan. 9, 2012.
Non-Final Office Action for U.S. Appl. No. 12/182,165, mailed Jan. 5, 2012.
Final Office Action for U.S. Appl. No. 11/701,799, mailed Feb. 13, 2012.
Non-Final Office Action for U.S. Appl. No. 12/581,582 mailed Mar. 14, 2012.
Final Office Action for U.S. Appl. No. 12/185,165 mailed Apr. 6, 2012.

* cited by examiner

DRUG DELIVERY COATING FOR USE WITH A STENT

RELATED APPLICATIONS

This application claims priority to, and the benefit of, co-pending U.S. Provisional Application Ser. No. 60/613,745, filed Sep. 28, 2004, for all subject matter common to both applications. The disclosure of said provisional application is hereby incorporated herein by reference in its entirety.

FIELD OF THE INVENTION

The present invention relates to coatings suitable for application to medical devices for delivery of one or more biologically active agents, and more particularly to a bio-absorbable coating able to provide controlled short or long term release of biologically active components from the surface of an implanted medical device or prosthesis.

BACKGROUND OF THE INVENTION

Therapeutic agents may be delivered to a targeted location in a human utilizing a number of different methods. For example, agents may be delivered nasally, transdermally, intravenously, orally, or via other conventional methods. Delivery may vary by release rate (i.e., quick release or slow release). Delivery may also vary as to how the drug is administered. Specifically, a drug may be administered locally to a targeted area, or administered systemically.

With systemic administration, the therapeutic agent is administered in one of a number of different ways including orally, inhallationally, or intravenously to be systemically processed by the patient. However, there are drawbacks to systemic delivery of a therapeutic agent, one of which is that high concentrations of the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

An alternative to the systemic administration of a therapeutic agent is the use of a targeted local therapeutic agent delivery approach. With local delivery of a therapeutic agent, the therapeutic agent is administered using a medical device or apparatus, directly by hand, or sprayed on the tissue, at a selected targeted tissue location of the patient that requires treatment. The therapeutic agent emits, or is otherwise delivered, from the medical device apparatus, and/or carrier, and is applied to the targeted tissue location. The local delivery of a therapeutic agent enables a more concentrated and higher quantity of therapeutic agent to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

Local delivery is often carried out using a medical device as the delivery vehicle. One example of a medical device that is used as a delivery vehicle is a stent. Boston Scientific Corporation sells the Taxus® stent, which contains a polymeric coating for delivering Paclitaxel. Johnson & Johnson, Inc. sells the Cypher® stent which includes a polymeric coating for delivery of Sirolimus.

Targeted local therapeutic agent delivery using a medical device can be further broken into two categories, namely, short term and long term. The short term delivery of a therapeutic agent occurs generally within a matter of seconds or minutes to a few days or weeks. The long term delivery of a therapeutic agent occurs generally within several weeks to a number of months. Typically, to achieve the long term delivery of a therapeutic agent, the therapeutic agent must be combined with a delivery agent, or otherwise formed with a physical impediment as a part of the medical device, to slow the release of the therapeutic agent.

U.S. patent Publication No. 2003/0204168 is directed to the local administration of drug combinations for the prevention and treatment of vascular disease. The publication discusses using intraluminal medical devices having drugs, agents, and/or compounds affixed thereto to treat and prevent disease and minimize biological reactions to the introduction of the medical device. The publication states that both bio-absorbable and biostable compositions have been reported as coatings for stents. They have been polymeric coatings that either encapsulate a pharmaceutical/therapeutic agent or drug, e.g. rapamycin, taxol etc., or bind such an agent to the surface, e.g. heparin-coated stents. These coatings are applied to the stent in a number of ways, including, though not limited to, dip, spray, or spin coating processes.

The publication goes on to state that although stents prevent at least a portion of the restenosis process, a combination of drugs, agents or compounds which prevents smooth muscle cell proliferation, reduces inflammation and reduces thrombosis or prevents smooth muscle cell proliferation by multiple mechanisms, reduces inflammation and reduces thrombosis combined with a stent may provide the most efficacious treatment for post-angioplasty restenosis. The systemic use of drugs, agents or compounds in combination with the local delivery of the same or different drug/drug combinations may also provide a beneficial treatment option.

The invention subsequently described in the '168 publication relates to the provision of polymeric coatings comprising a polyfluoro copolymer and implantable medical devices, for example, stents coated with a film of the polymeric coating in amounts effective to reduce thrombosis and/or restenosis when such stents are used in, for example, angioplasty procedures. Blends of polyfluoro copolymers are also used to control the release rate of different agents or to provide a desirable balance of coating properties, i.e. elasticity, toughness, etc., and drug delivery characteristics, for example, release profile. Polyfluoro copolymers with different solubilities in solvents may be used to build up different polymer layers that may be used to deliver different drugs or to control the release profile of a drug.

The coatings and drugs, agents or compounds described are described as being useful in combination with any number of medical devices, and in particular, with implantable medical devices such as stents and stent-grafts. Other devices such as vena cava filters and anastomosis devices may be used with coatings having drugs, agents, or compounds therein.

U.S. Pat. No. 6,358,556 is directed to a drug release stent coating. The patent describes processes for producing a relatively thin layer of biostable elastomeric material in which an amount of biologically active material is dispersed as a coating on the surfaces of a deployable stent. The coating is described as preferably being applied as a mixture, solution, or suspension of polymeric material and finely divided biologically active species dispersed in an organic vehicle or a solution or partial solution of such species in a solvent or vehicle for the polymer and/or biologically active species. Essentially the active material is dispersed in a carrier material that may be a polymer, a solvent, or both.

U.S. Pat. No. 6,299,604 is directed to a coated implantable medical device having a layer of bioactive material and a coated layer providing controlled release of the bioactive material. The patent discusses the idea that the degradation of an agent, a drug, or a bioactive material, applied to an implantable medical device may be avoided by covering the agent, drug, or bioactive material, with a porous layer of a biocompatible polymer that is applied without the use of solvents, catalysts, heat or other chemicals or techniques, which would otherwise be likely to degrade or damage the agent, drug or material. Those biocompatible polymers may be applied preferably by vapor deposition or plasma deposition, and may polymerize and cure merely upon condensation from the vapor phase, or may be photolytically polymerizable and are expected to be useful for this purpose. As such, this patent focuses on the use of polymers to act as drug delivery agents in providing a controlled release of a drug from an implanted medical device.

U.S. Publication No. 2003/0004564 is directed to a drug delivery platform. The publication describes compositions and methods for a stent based drug delivery system. The stent comprises a matrix, where the matrix has entrapped a pharmaceutical agent of interest. The matrix, for example microspheres, etc. resides within a channel formed on one or both of the abluminal or adluminal surfaces of the stent, and allows for release, usually sustained release, of the entrapped agent. The stent and matrix is encased with a gel covalently bound to the stent surface and optionally also covalently bound to the matrix, which prevents loss of the matrix during transport and implantation of the stent, and which affects the release of the biologically active agent, through degradation and diffusion characteristics. The matrix is described as a biodegradable, bioerodible, or biocompatible non-biodegradable matrix comprising a biologically active agent that is placed within the channels of the stent surface. The matrix may be of any geometry including fibers, sheets, films, microspheres, circular discs, plaques and the like. The gel is selected to be a polymeric compound that will fill the spaces between the matrix and the channel, that can be covalently bound to the stent surface and optionally covalently bound to the matrix, and that provides a porous protective barrier between the matrix and the environment, for example during storage, implantation, flow conditions, etc. The gel may contribute to the control of drug release through its characteristics of degradation and diffusion.

U.S. Pat. No. 4,952,419 is directed to a method of making antimicrobial coated implant devices. The reference discusses the desire to have better retention of coatings on the implant surface during mechanized implant packaging operations. The solution presented involves the use of a silicone fluid in contact with the surface of the implant and an antimicrobial agent in contact with the silicone fluid. There is no discussion of any therapeutic benefit inherent in the silicone fluid itself, and there is no suggestion that other oils can be utilized to control the delivery of the antimicrobial agent The above-described references fail to teach or suggest the use of bio-absorbable fats or oils in any form as the drug delivery platform. In each instance, the drug delivery platform includes the use of a form of polymeric material, or silicone material, with a solvent additive. The polymeric material serves as either a base upon which a drug coating is applied, a substance mixed in with the drug to form the coating, or a top coating applied over a previously applied drug coating to control the release of the drug.

PCT application publication No. WO 00/62830 is directed to a system and method for coating medical devices using air suspension. The technique involves suspending a medical device in an air stream and introducing a coating material into the air stream such that the coating material is dispersed therein and coats the medical device. The publication discusses applying the coating to a number of different medical devices formed of a number of different materials. The publication further suggests that the coating materials can be comprised of therapeutic agents alone or in combination with solvents, and that the coating may provide for controlled release, which includes long-term or sustained release. As stated in the publication, a list of coating materials other than therapeutic agents include polymeric materials, sugars, waxes, and fats applied alone or in combination with therapeutic agents, and monomers that are cross-linked or polymerized. The publication goes on to discuss the use of a drug matrix formed of a polymer structure, which can be used to control the release rate of drugs combined with the polymer.

Although the '830 publication attempts to discuss every possible combination of delivery coating in combination with every drug or therapeutic agent that may have some utility in targeted delivery applications, there is no realization of the difficulty of using an oil for the controlled release of a therapeutic agent in a long term application. A list of potential delivery vehicles identifies waxes and fats, however there is no indication that such vehicles can be utilized for anything other than a short term drug delivery. A later discussion of controlled long term release of a drug mentions only the use of polymers to control the release.

U.S. Pat. No. 6,117,911 is directed to the use of compounds and different therapies for the prevention of vascular and non-vascular pathologies. The '911 patent discusses the possibility of using many different types of delivery methods for a therapeutic agent or agents to prevent various vascular and non-vascular pathologies. One such approach is described as providing a method of preventing or treating a mammal having, or at risk of developing, atherosclerosis, including administering an amount of a combination of aspirin or an aspirinate and at least one omega-3 fatty acid, wherein said amount of omega-3 fatty acid is effective to maintain or increase the level of TGF-beta so as to provide a synergistic effect with a therapeutic compound to inhibit or reduce vessel lumen diameter dimension. As such, the patent discusses some of the therapeutic benefits of primarily systemic administration of omega-3 fatty acids to affect TGF-beta levels when a therapeutic agent is combined with aspirin or aspirinate. That is, the dose or concentration of omega-3-fatty acid required to increase the level of TGF-beta is significantly greater, requiring long term systemic delivery.

PCT Application Publication No. WO 03/028622 is directed to a method of delivering drugs to a tissue using drug coated medical devices. The drug coated medical device is brought into contact with the target tissue or circulation and the drugs are quickly released onto the area surrounding the device in a short period of time after contact is made. The release of the drug may occur over a period of 30 seconds, 1 minute or 3 minutes. In one embodiment described in the publication, the carrier of the drug is a liposome. Other particles described as potential drug carriers include lipids, sugars, carbohydrates, proteins, and the like. The publication describes these carriers as having properties appropriate for a quick short term release of a drug combined with the carriers.

PCT application publication No. WO 02/100455 is directed to ozonated medical devices and methods of using ozone to prevent complications from indwelling medical devices. The application discusses having the ozone in gel or liquid form to coat the medical device. The ozone can be dissolved in olive oil, or other types of oil, to form a gel containing ozone bubbles, and the gel applied to the medical device as a coating. The application later asserts a preference for the gel or other coating formulation to be composed so that the ozone is released over time. However, there is no indication in the application as to how a slow controlled release of ozone can be affected. There is no enablement to a long term controlled release of ozone from the olive oil gel, however, there is mention of use of biocompatible polymers to form the coating that holds and releases the ozone. Other drugs are also suggested for combination with the ozone for delivery to a targeted location. The application later describes different application methods for the coating, including casting, spraying, painting, dipping, sponging, atomizing, smearing, impregnating, and spreading.

U.S. Pat. No. 5,509,899 is directed to a medical device having a lubricious coating. In the background section of this patent, it states that catheters have been rendered lubricious by coating them with a layer of silicone, glycerin, or olive oil in the past. It further states that such coatings are not necessarily satisfactory in all cases because they tend to run off and lose the initial lubricity rather rapidly and they can also lack abrasion resistance. Hydrophilic coatings have also been disclosed such as polyvinyl pyrrolidone with polyurethane interpolymers or hydrophilic polymer blends of thermoplastic polyurethane and polyvinyl pyrrolidone. Accordingly, the invention in the '899 patent is described as providing a biocompatible surface for a device which can impede blocking or sticking of two polymer surfaces when the surfaces are placed in tight intimate contact with each other such as is the case when the balloon is wrapped for storage or when a surface of one device will contact a surface of another device. The description goes on to describe numerous polymeric substances.

European Patent Application No. EP 1 273 314 is directed to a stent having a biologically and physiologically active substance loaded onto the stent in a stable manner. The biologically and physiologically active substance is gradually released over a prolonged period of time with no rapid short term release. In order to achieve the long term controlled release, the application describes placing a layer of the biologically and physiologically active substance on the surface of the stent, and placing a polymer layer on top of the biologically and physiologically active substance layer. The polymer layer acts to slow the release of the biologically and physiologically active substance. There is no discussion of an alternative to the polymer substance forming the polymer layer for controlling the release of the biologically and physiologically active substance. There are instances discussed when the biologically and physiologically active substance has insufficient adhesion characteristics to adhere to the stent. In such instances, the application describes using an additional substance mixed with the biologically and physiologically active substance to increase its adhesion properties. In the case of a fat soluble substance, the recommendation is the use of a low molecular weight fatty acid having a molecular weight of up to 1000, such as fish oil, vegetable oil, or a fat-soluble vitamin such as vitamin A or vitamin E. The application always requires use of the additional polymer coating to create the long term controlled release of the biologically and physiologically active substance.

A paper entitled "Evaluation of the Biocompatibility and Drug Delivery Capabilities of Biological Oil Based Stent Coatings", by Shengqiao Li of the Katholieke Universiteit Leuven, discusses the use of biological oils as a coating for delivering drugs after being applied to stents. Three different coatings were discussed, a glue coating (cod liver oil mixed with 100% ethanol at a 1:1 ratio), a vitamin E coating (97% vitamin E oil solution mixed with 100% ethanol at a 1:1 ratio), and a glue+vitamin E coating (cod liver oil and 97% vitamin E oil solution mixed with 100% ethanol at a 1:1 ratio). Bare stents and polymer coated stents, along with stents having each of the above coatings, were implanted into test subjects, and analyzed over a four week period. At the end of the period, it was observed that the bare stents and polymer coated stents resulted in some minor inflammation of the tissue. The main finding of the study was that the glue coatings have a good biocompatibility with coronary arteries, and that the glue coating does not affect the degree of inflammation, thrombosis, and neointimal proliferation after endovascular stenting compared with the conventional stenting approach. A further hypothesis asserted was that the oil coating provided lubrication to the stent, thus decreasing the injury to the vascular wall.

The study went on to analyze the drug loading capacity of biological oil based stent coatings. Balloon mounted bare stents were dip-coated in a biological oil solution with the maximal solublizable amount of different drugs (a separate drug for each trial), and compared with polymer coated, drug loaded, stents. According to the release rate curves, there was a clear indication that drug release was fast in the first 24 hours with more than 20% of the drug released, for the oil based coatings. The release rate after the first 24 hours was much slower, and continued for a period up to about six weeks.

Another aspect of the study looked at the efficacy of drug loaded biological stents to decrease inflammation and neointimal hyperplasia in a porcine coronary stent model. In this part of the study, glue or modified glue (biological oil) coated stainless steel stents were loaded with different drugs. The result was that the characteristics of the particular drug loaded onto the stent were the major factor to the reduction of restenosis, and the biological oil did not have a major impact on either causing or reducing inflammation.

A further comment indicated that in the studies comparison was made between biological oil based drug loaded stents and bare stents to find differences in inflammation, injury, and hyperplasia. Inflammation, injury, and neointimal hyperplasia resulted in in-stent area stenosis. Any anti-inflammation observed was the result of the particular drug loaded on the stent, regardless of biological oil, or polymer, coating.

PCT Application Publication No. WO 03/039612 is directed to an intraluminal device with a coating containing a therapeutic agent. The publication describes coating an intraluminal device with a therapeutic agent comprised of a matrix that sticks to the intraluminal device. The matrix is formed of a bio-compatible oil or fat, and can further include alfa-tocopherol. The publication further indicates that an oil or fat adheres sufficiently strongly to the intraluminal device so that most of the coating remains on the intraluminal device when it is inserted in a body lumen. The publication further states that the oil or fat slows the release of the therapeutic agent, and also acts as an anti-inflammatory and a lubricant. The publication goes on to indicate that the oil or fat can be chemically modified, such as by the process of hydrogenation, to increase their melting point. Alternatively, synthetic oils could be manufactured as well. The oil or fat is further noted to contain fatty acids.

The '612 publication provides additional detail concerning the preferred oil or fat. It states that a lower melting point is preferable, and a melting point of 0° C. related to the oils utilized in experiments. The lower melting point provides a fat in the form of an oil rather than a wax or solid. It is further stated that oils at room temperature can be hydrogenated to provide a more stable coating and an increased melting point, or the oils can be mixed with a solvent such as ethanol. Preferences were discussed for the use of oils rather than waxes or solids, and the operations performed on the fat or oil as described can be detrimental to the therapeutic characteristics of some oils, especially polyunsaturated oils containing omega-3 fatty acids.

U.S. Publication No. 2003/0083740 similarly discusses the use of certain oils as a matrix for delivery of drugs. More specifically, this publication is directed to a method for forming liquid coatings for medical devices such as stents and angioplasty balloons. The liquid coatings can be made from biodegradable materials in liquid, low melting solid, or wax forms, which preferably degrade in the body without producing potentially harmful fragments. These fragments occur with harder coatings that fracture and break off after implantation. The liquid coatings may also contain biologically active components, such as drugs, which are released from the coatings through diffusion from the coatings and the degradation of the coatings.

Some of this second group of references do refer to the use of oils as a drug delivery platform. However, there is no realization of the difficulty of using an oil for the controlled release of a therapeutic agent in a long term application. There is further no indication that the coatings described in the above references are bio-absorbable, while also providing a controlled release of biologically active components, such as drugs. For controlled release of a drug, the above references require use of a polymer based coating either containing the drug or applied over the drug on the medical device.

What is desired is a bio-absorbable delivery agent having non-inflammatory characteristics that is able to be prepared in combination with at least one therapeutic agent for the delivery of that therapeutic agent to body tissue in a long term controlled release manner.

SUMMARY OF THE INVENTION

There is a need for a bio-absorbable coating for application to an implantable medical device for therapeutic purposes. The present invention is directed toward further solutions to address this need.

In accordance with one embodiment of the present invention, a coated medical device includes a coating having a bio-absorbable carrier component, the bio-absorbable carrier component being at least partially formed of a cellular uptake inhibitor and a cellular uptake enhancer. The coating further includes a solubilized or dispersed therapeutic agent. The coated medical device is implantable in a patient to effect controlled delivery of the therapeutic agent to the patient. The controlled delivery is at least partially characterized by total and relative amounts of the cellular uptake inhibitor and cellular uptake enhancer in the bio-absorbable carrier component.

In accordance with aspects of the present invention, the bio-absorbable carrier component contains lipids. The bio-absorbable carrier component can be a naturally occurring oil, such as fish oil. The bio-absorbable carrier component can be modified from its naturally occurring state to a state of increased viscosity in the form of a cross-linked gel. The bio-absorbable carrier component can contain omega-3 fatty acids.

It should be noted that as utilized herein, the term fish oil fatty acid includes but is not limited to omega-3 fatty acid, fish oil fatty acid, free fatty acid, triglycerides, or a combination thereof. The fish oil fatty acid includes one or more of arachidic acid, gadoleic acid, arachidonic acid, eicosapentaenoic acid, docosahexaenoic acid or derivatives, analogs and pharmaceutically acceptable salts thereof. Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof.

It should be noted that the term cross-linked gel, as utilized herein with reference to the present invention, refers to a gel that is non-polymeric and is derived from an oil composition comprising molecules covalently cross-linked into a three-dimensional network by one or more of ester, ether, peroxide, and carbon-carbon bonds in a substantially random configuration. In various preferred embodiments, the oil composition comprises a fatty acid molecule, a glyceride, and combinations thereof.

In accordance with further aspects of the present invention the therapeutic agent component mixes with the bio-absorbable carrier component. The therapeutic agent component can include an agent selected from the group consisting of anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, antiseptics, proteoglycans, GAG's, gene delivery (polynucleotides), antifibrotics, analgesics, prodrugs, polysaccharides (e.g., heparin), anti-migratory agents, pro-healing agents, and ECM/protein production inhibitors. The therapeutic agent component can alternatively take the form of an agent selected from the group consisting of cerivastatin, cilostazol, fluvastatin, lovastatin, paclitaxel, pravastatin, rapamycin, and simvastatin. The coating can be bio-absorbable, inhibit restenosis, and/or be non-polymeric.

In accordance with further aspects of the present invention, the coating can optionally include a solvent. The solvent can be Ethanol, N-Methyl-2-Pyrrolidone (NMP), or some other solvent compatible with the coating, therapeutic agent, and intended use. The coating can further include a compatibilizer, such as vitamin E or its derivatives, which also acts as a stabilizer and/or preservative, therapeutic agent, antioxidant, thickener, or tactifyer.

It should be noted that as utilized herein to describe the present invention, the term vitamin E and the term alpha-tocopherol, are intended to refer to the same or substantially similar substance, such that they are interchangeable and the use of one includes an implicit reference to both. Further included in association with the term vitamin E are such variations including but not limited to one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof. It should also be noted that other antioxidants may be used as a substitute to fulfill the functions of Vitamin E in this coating.

In accordance with further aspects of the present invention, the medical device can be a stent. The stent can be formed of a metal. The stent can further be formed of a substance selected from the group consisting of stainless steel, Nitinol alloy, nickel alloy, titanium alloy, cobalt-chromium alloy, ceramics, plastics, and polymers.

In accordance with further aspects of the present invention, the surface of the medical device can be provided with a surface preparation prior to the application of the coating comprising the bio-absorbable carrier component. The pre-treatment, or preparation of the surface, improves coating conformability and consistency and enhances the adhesion of the coating comprising the bio-absorbable carrier component. The pre-treatment can be bio-absorbable, and can contain lipids. The pre-treatment can be a naturally occurring oil, such as fish oil, and can be modified from its naturally occurring state to state of increased viscosity in the form of a cross-linked gel. The pre-treatment can contain omega-3 fatty acids.

In accordance with one embodiment of the present invention, a method of making a coated medical device includes providing the medical device. A coating is applied, the coating including a bio-absorbable carrier component. The coated medical device is implantable in a patient to effect controlled delivery of the coating to the patient.

In accordance with another embodiment of the present invention, a method of making a coated medical device includes providing the medical device. A coating is applied having a bio-absorbable carrier component, the bio-absorbable carrier component being at least partially formed of a cellular uptake inhibitor and a cellular uptake enhancer. The coating further includes a solubilized or dispersed therapeutic agent. The coated medical device is implantable in a patient to effect controlled delivery of the therapeutic agent to the patient. The controlled delivery is at least partially characterized by total and relative amounts of the cellular uptake inhibitor and cellular uptake enhancer in the bio-absorbable carrier component.

In accordance with aspects of the present invention, the bio-absorbable carrier component can contain lipids, and can be naturally occurring oil, such as fish oil.

In accordance with aspects of the present invention, the method can further include modifying the bio-absorbable carrier component from its naturally occurring state to a state of increased viscosity in the form of a cross-linked gel. The bio-absorbable carrier component can contain omega-3 fatty acids.

In accordance with further aspects of the present invention, the method can further include providing the coating with a therapeutic agent component. The therapeutic agent component mixes with the bio-absorbable carrier component. The coating can be bio-absorbable, can inhibit restenosis, and/or can be non-polymeric.

In accordance with further aspects of the present invention, the method can further include providing a solvent mixed with the bio-absorbable carrier to form the coating. The solvent can be Ethanol, NMP, or other solvent compatible with the coating and the therapeutic component. The method can further include providing a compatibilizer, such as vitamin E, which also acts as a stabilizer and preservative during formation of the coating. Alternatively, the solvent can be removed with vacuum or heat.

The medical device coating using the method can be a stent. The stent can be formed of a metal, or other substance such as stainless steel, Nitinol alloy, nickel alloy, titanium alloy, cobalt-chromium alloy, ceramics, plastics, and polymers.

In accordance with further aspects of the present invention, the method can further include providing a surface preparation or pre-treatment on the surface of the medical device prior to application of the coating comprising the bio-absorbable carrier component, wherein the pre-treatment improves the coating consistency and conformability and enhances the adhesion of the coating comprising the bio-absorbable carrier component. The pre-treatment can be bio-absorbable, contain lipids, and/or take the form of a naturally occurring oil, such as fish oil. The pre-treatment can be modified from its natural state to a state of increased viscosity in the form of a cross-linked gel. The pre-treatment can likewise contain omega-3 fatty acids.

In accordance with another embodiment of the present invention, a method of making a coated medical device includes providing the medical device. A coating is applied to the medical device having a bio-absorbable carrier component and a therapeutic agent component. The coated medical device is implantable in a patient to effect controlled delivery of the coating to the patient.

In accordance with one aspect of the present invention, the method can further include preparing the coating prior to application to the medical device. Preparing the coating can include mixing vitamin E and the bio-absorbable carrier component to form a first mixture. Solvent and the therapeutic agent component are mixed to form a second mixture. The first mixture and the second mixture are then mixed to form a coating substance. The first mixture and the second mixture can be created independently and interchangeably first, second, or substantially simultaneously.

In accordance with further aspects of the present invention, the step of applying the coating can include at least one of dipping the medical device in the coating substance, spraying the coating substance on the medical device, brushing the coating substance on the medical device, swabbing the coating substance on the medical device, painting the coating substance on the medical device, wiping the coating substance on the medical device, printing the coating substance on the medical device, and electrostatically applying the coating substance to the medical device, with or without an applicator.

The method can further includes curing the coating on the medical device. Curing can involve applying at least one of heat, UV light, chemical cross-linker, or reactive gas to cure the coating. Curing with respect to the present invention generally refers to thickening, hardening, or drying of a material brought about by heat, UV, or chemical means.

The method can further include sterilizing the coating and the medical device. Sterilization can involve use of at least one of ethylene oxide, gamma radiation, e-beam, steam, gas plasma, and vaporized hydrogen peroxide (VHP).

The method can further include providing a surface preparation or pre-treatment on the surface of the medical device prior to application of the coating comprising the bio-absorbable carrier component, wherein the pre-treatment improves the coating consistency and conformability and enhances the adhesion of the coating comprising the bio-absorbable carrier component. The pre-treatment can be bio-absorbable, and/or can be a naturally occurring oil, such as fish oil.

BRIEF DESCRIPTION OF THE DRAWINGS

The aforementioned features and advantages, and other features and aspects of the present invention, will become better understood with regard to the following description and accompanying drawings, wherein.

DETAILED DESCRIPTION

Figure 1:
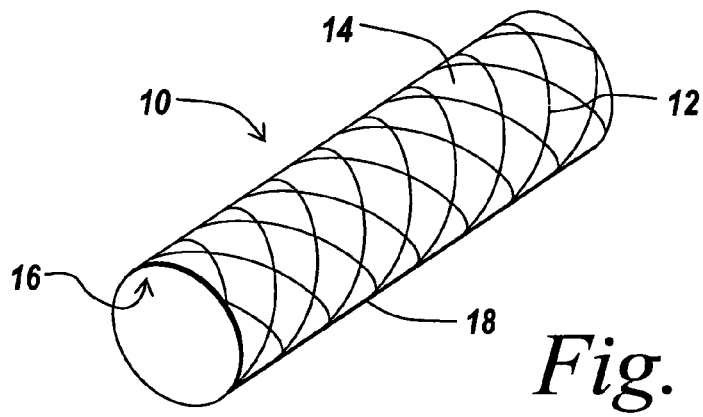
FIG. 1 is a diagrammatic illustration of a medical device, according to one embodiment of the present invention.

An illustrative embodiment of the present invention relates to the provision of a coating on an implantable medical device. The coating includes a bio-absorbable carrier component. In addition to the bio-absorbable carrier component, a therapeutic agent component can also be provided. The coated medical device is implantable in a patient to effect controlled delivery of the coating to the patient.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance is soluble in the phospholipid bi-layer of cells of body tissue, and therefore impacts how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes, in a manner that does not result in cellular uptake of the biodegradable substance. Biodegradation thus relates to the breaking down and distributing of a substance through the patient's body, verses the penetration of the cells of the patient's body tissue. Biodegradable substances can cause inflammatory response due to either the parent substance or those formed during breakdown, and they may or may not be absorbed by tissues.

The phrase "controlled release" generally refers to the release of a biologically active agent in a predictable manner over the time period of weeks or months, as desired and predetermined upon formation of the biologically active agent on the medical device from which it is being released. Controlled release includes the provision of an initial burst of release upon implantation, followed by the predictable release over the aforementioned time period.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

Oil that is hydrogenated becomes a waxy solid. Attempts have been made to convert the polyunsaturated oils into a wax or solid to allow the oil to adhere to a device for a longer period of time. One such approach is known as hydrogenation, which is a chemical reaction that adds hydrogen atoms to an unsaturated fat (oil) thus saturating it and making it solid at room temperature. This reaction requires a catalyst, such as a heavy metal, and high pressure. The resultant material forms a non-cross-linked semi-solid. Hydrogenation can reduce or eliminate omega-3 fatty acids, and any therapeutic effects (both anti-inflammatory and wound healing) they offer.

In addition, some curing methods have been indicated to have detrimental effects on the therapeutic agent combined with the omega-3 fatty acid, making them partially or completely ineffective. As such, oils, and more specifically oils containing omega-3 fatty acids, have been utilized as a delivery agent for the short term uncontrolled release of a therapeutic agent, so that minimal or no curing is required. However, there are no known uses of oils containing omega-3 fatty acids for combination with a therapeutic agent in a controlled release application that makes use of the therapeutic benefits of the omega-3 fatty acids. Further, some heating of the omega-3 fatty acids to cure the oil can lessen the total therapeutic effectiveness of the omega-3 fatty acids, but not eliminate the therapeutic effectiveness. One characteristic that can remain after certain curing by heating methods is the non-inflammatory response of the tissue when exposed to the cured material. As such, an oil containing omega-3 fatty acids can be heated for curing purposes, and still maintain some or even a substantial portion of the therapeutic effectiveness of the omega-3 fatty acids. In addition, although the therapeutic agent combined with the omega-3 fatty acid and cured with the omega-3 fatty acid can be rendered partially ineffective, the portion remaining of the therapeutic agent can, in accordance with the present invention, maintain pharmacological activity and in some cases be more effective than an equivalent quantity of agent delivered with other coating delivery agents. Thus, if for example, 80% of a therapeutic agent is rendered ineffective during curing, the remaining 20% of therapeutic agent, combined with and delivered by the coating can be efficacious in treating a medical disorder, and in some cases have a relatively greater therapeutic effect than the same quantity of agent delivered with a polymeric or other type of coating.

For long term controlled release applications, polymers, as previously mentioned, have been utilized in combination with a therapeutic agent. Such a combination provides a platform for the controlled long term release of the therapeutic agent from a medical device. However, polymers have been determined to themselves cause inflammation in body tissue. Therefore, the polymers often must include at least one therapeutic agent that has an anti-inflammatory effect to counter the inflammation caused by the polymer delivery agent. In addition, patients that received a polymer-based implant must also follow a course of long term systemic anti-platelet therapy, on a permanent basis, to offset the thrombogenic properties of the non-absorbable polymer. A significant percentage of patients that receive such implants are required to undergo additional medical procedures, such as surgeries (whether related follow-up surgery or non-related surgery) and are required to stop their anti-platelet therapy. This can lead to a thrombotic event, such as stroke, which can lead to death. Use of the inventive coating described herein can negate the necessity of anti-platelet therapy, and the corresponding related risks described, because there is no thrombogenic polymer reaction to the coating.

FIGS. 1 through 13, wherein like parts are designated by like reference numerals throughout, illustrate an example embodiment of a coated medical device according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 illustrates a stent 10 in accordance with one embodiment of the present invention. The stent 10 is representative of a medical device that is suitable for having a coating applied thereon to effect a therapeutic result. The stent 10 is formed of a series of interconnected struts 12 having gaps 14 formed therebetween. The stent 10 is generally cylindrically shaped. Accordingly, the stent 10 maintains an interior surface 16 and an exterior surface 18.

One of ordinary skill in the art will appreciate that the illustrative stent 10 is merely exemplary of a number of different types of stents available in the industry. For example, the strut 12 structure can vary substantially. The material of the stent can also vary from a metal, such as stainless steel, Nitinol, nickel, and titanium alloys, to cobalt chromium alloy, ceramic, plastic, and polymer type materials. One of ordinary skill in the art will further appreciate that the present invention is not limited to use on stents. Instead, the present invention has application on a wide variety of medical devices. For purposes of clarity, the following description will refer to a stent as the exemplar medical device. The terms medical device and stent are interchangeable with regard to the applicability of the present invention. Accordingly, reference to one or another of the stent, or the medical device, is not intended to unduly limit the invention to the specific embodiment described.

Figure 2:
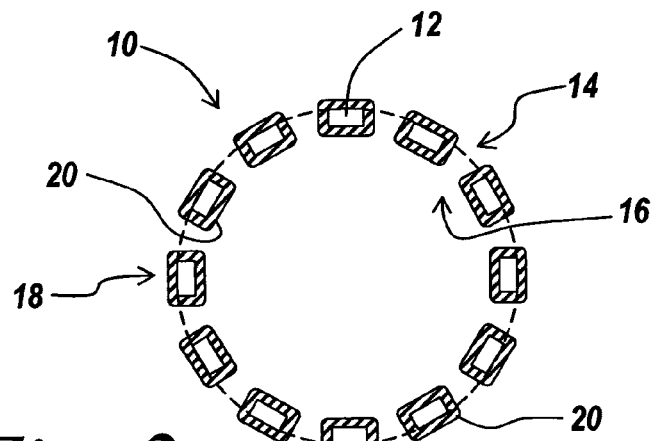
FIG. 2 is a cross-sectional view of the medical device in accordance with one aspect of the present invention.
Figure 3:
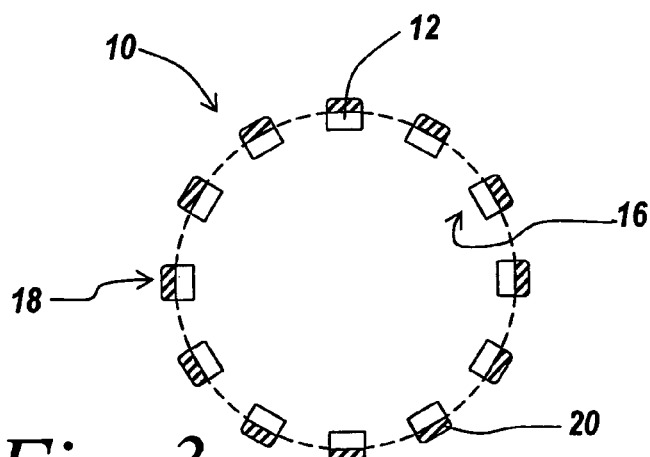
FIG. 3 is a cross-sectional view of the medical device in accordance with another aspect of the present invention.

FIG. 2 illustrates one example embodiment of the stent 10 having a coating 20 applied thereon in accordance with the present invention. FIG. 3 is likewise an alternative embodiment of the stent 10 having the coating 20 also applied thereon. The coating 20 is applied to the medical device, such as the stent 10, to provide the stent 10 with different surface properties, and also to provide a vehicle for therapeutic applications.

In FIG. 2, the coating 20 is applied on both the interior surface 16 and the exterior surface 18 of the strut 12 forming the stent 10. In other words, the coating 20 in FIG. 2 substantially encapsulates the struts 12 of the stent 10. In FIG. 3, the coating 20 is applied only on the exterior surface 18 of the stent 10, and not on the interior surface 16 of the stent 10. The coating 20 in both configurations is the same coating; the difference is merely the portion of the stent 10 that is covered by the coating 20. One of ordinary skill in the art will appreciate that the coating 20 as described throughout the Description can be applied in both manners shown in FIG. 2 and FIG. 3, in addition to other configurations such as, partially covering select portions of the stent 10 structure. All such configurations are described by the coating 20 reference.

In accordance with embodiments of the present invention, the stent 10 includes the coating 20, which is bio-absorbable. The coating 20 has a bio-absorbable carrier component, and can also include a therapeutic agent component that can also be bio-absorbable. When applied to a medical device such as a stent 10, it is often desirable for the coating to inhibit or prevent restenosis. Restenosis is a condition whereby the blood vessel experiences undesirable cellular remodeling after injury. When a stent is implanted in a blood vessel, and expanded, the stent itself may cause some injury to the blood vessel. The treated vessel typically has a lesion present which can contribute to the inflammation and extent of cellular remodeling. The end result is that the tissue has an inflammatory response to the conditions. Thus, when a stent is implanted, there is often a need for the stent to include a coating that inhibits inflammation, or is non-inflammatory, and prevents restenosis. These coatings have been provided using a number of different approaches as previously described in the Background. However, none of the prior coatings have utilized a bio-absorbable carrier component to create a bio-absorbable coating with suitable non-inflammatory properties for controlled release of a therapeutic agent.

In accordance with one embodiment of the present invention, the bio-absorbable carrier component is in the form of a naturally occurring oil. An example of a naturally occurring oil is fish oil or cod liver oil. A characteristic of the naturally occurring oil is that the oil includes lipids, which contributes to the lipophilic action described later herein, that is helpful in the delivery of therapeutic agents to the cells of the body tissue. In addition, the naturally occurring oil includes omega-3 fatty acids in accordance with several embodiments of the present invention. As previously described, omega-3 fatty acids and omega-6 fatty acids are known as essential fatty acids. Omega-3 fatty acids can be further characterized as eicosapentaenoic acid (EPA), docosahexanoic acid (DHA), and alpha-linolenic acid (ALA). Both EPA and DHA are known to have anti-inflammatory effects and wound healing effects within the human body.

In further detail, the term "bio-absorbable" generally refers to having the property or characteristic of being able to penetrate the tissues of a patient's body. In example embodiments of the present invention, the bio-absorbable coating contains lipids, many of which originate as triglycerides. It has previously been demonstrated that triglyceride products such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Vitamin E compounds can also integrate into cellular membranes resulting in decreased membrane fluidity and cellular uptake.

It is also known that damaged vessels undergo oxidative stress. A coating containing an antioxidant such as alpha-tocopherol may aid in preventing further damage by this mechanism.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol are accommodated by the coating of the present invention described herein. Accordingly, fatty acids and alpha-tocopherol can be combined in differing amounts and ratios to contribute to a coating in a manner that provides control over the cellular uptake characteristics of the coating and any therapeutic agents mixed therein.

It should further be emphasized that the bio-absorbable nature of the carrier component and the resulting coating (in the instances where a bio-absorbable therapeutic agent component is utilized) results in the coating 20 being completely absorbed over time by the cells of the body tissue. There are no substances in the coating, or break down products of the coating, that induce an inflammatory response. In short, the coating 20 is generally composed of fatty acids, including in some instances omega-3 fatty acids, bound to triglycerides, potentially also including a mixture of free fatty acids and vitamin E. The triglycerides are broken down by lipases (enzymes) which result in free fatty acids that can than be transported across cell membranes. Subsequently, fatty acid metabolism by the cell occurs to metabolize any substances originating with the coating. The bio-absorbable nature of the coating of the present invention thus results in the coating being absorbed, leaving only an underlying delivery or other medical device structure. There is no foreign body response to the bio-absorbable carrier component, including no inflammatory response. The modification of the oils from a more liquid physical state to a more solid, but still flexible, physical state is implemented through the curing process. As the oils are cured, especially in the case of fatty acid-based oils such as fish oil, cross-links form creating a gel. As the curing process is performed over increasing time durations and/or increasing temperature conditions, more cross-links form transitioning the gel from a relatively liquid gel to a relatively solid-like, but still flexible, gel structure.

As previously mentioned, the coating can also include a therapeutic agent component. The therapeutic agent component mixes with the bio-absorbable carrier component as described later herein. The therapeutic agent component can take a number of different forms including but not limited to anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, antiseptics, proteoglycans, GAG's, gene delivery (polynucleotides), polysaccharides (e.g., heparin), anti-migratory agents, pro-healing agents, ECM/protein production inhibitors, analgesics, prodrugs, and any additional desired therapeutic agents such as those listed in Table 1 below.

TABLE 1

| CLASS | EXAMPLES |
| --- | --- |
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibitation of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, |

TABLE 1-continued

| CLASS | EXAMPLES |
|---|---|
| | ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma -1b, Interluekin - 10 |
| Immunosuppressive/ Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in U.S. Patent Application Publication 2004/0235762), a rapamycin derivative (for example, as described in U.S. Pat. No. 6,200, 985), everolimus, seco-rapamycin, seco-everolimus, and simvastatin. Depending on the type of therapeutic agent component added to the coating, the resulting coating can be bio-absorbable if the therapeutic agent component is also bio-absorbable. As described in the Summary of the Invention, the present invention relates to coating a medical device such as the stent 10 with a coating such as coating 20. The coating 20 is formed of at least two primary components, namely a bio-absorbable carrier component and a therapeutic agent component. The therapeutic agent component has some form of therapeutic or biological effect. The bio-absorbable carrier component can also have a therapeutic or biological effect. It should again be noted that the bio-absorbable carrier component is different from the conventional bio-degradable substances utilized for similar purposes. The bio-absorbable characteristic of the carrier component enables the cells of body tissue of a patient to absorb the bio-absorbable carrier component itself, rather than breaking down the carrier component into inflammatory by-products and disbursing said by-products of the component for ultimate elimination by the patient's body. Accordingly, anti-inflammatory drug dosages to the patient do not need to be increased to additionally compensate for inflammation caused by the carrier component, as is otherwise required when using polymer-based carriers that themselves cause inflammation.

It should also be noted that the present description makes use of the stent 10 as an example of a medical device that can be coated with the coating 20 of the present invention. However, the present invention is not limited to use with the stent 10. Instead, any number of other implantable medical devices can be coated in accordance with the teachings of the present invention with the described coating 20. Such medical devices include catheters, grafts, balloons, prostheses, stents, other medical device implants, and the like. Implantation refers to both temporarily implantable medical devices, as well as permanently implantable medical devices. In the instance of the example stent 10, a common requirement of stents is that they include some substance or agent that inhibits restenosis. Accordingly, the example coating 20 as described is directed toward the reduction or the elimination of restenosis. However, one of ordinary skill in the art will appreciate that the coating 20 can have other therapeutic or biological benefits. The composition of the coating 20 is simply modified or mixed in a different manner to result in a different biological effect.

Figures 4, 5:
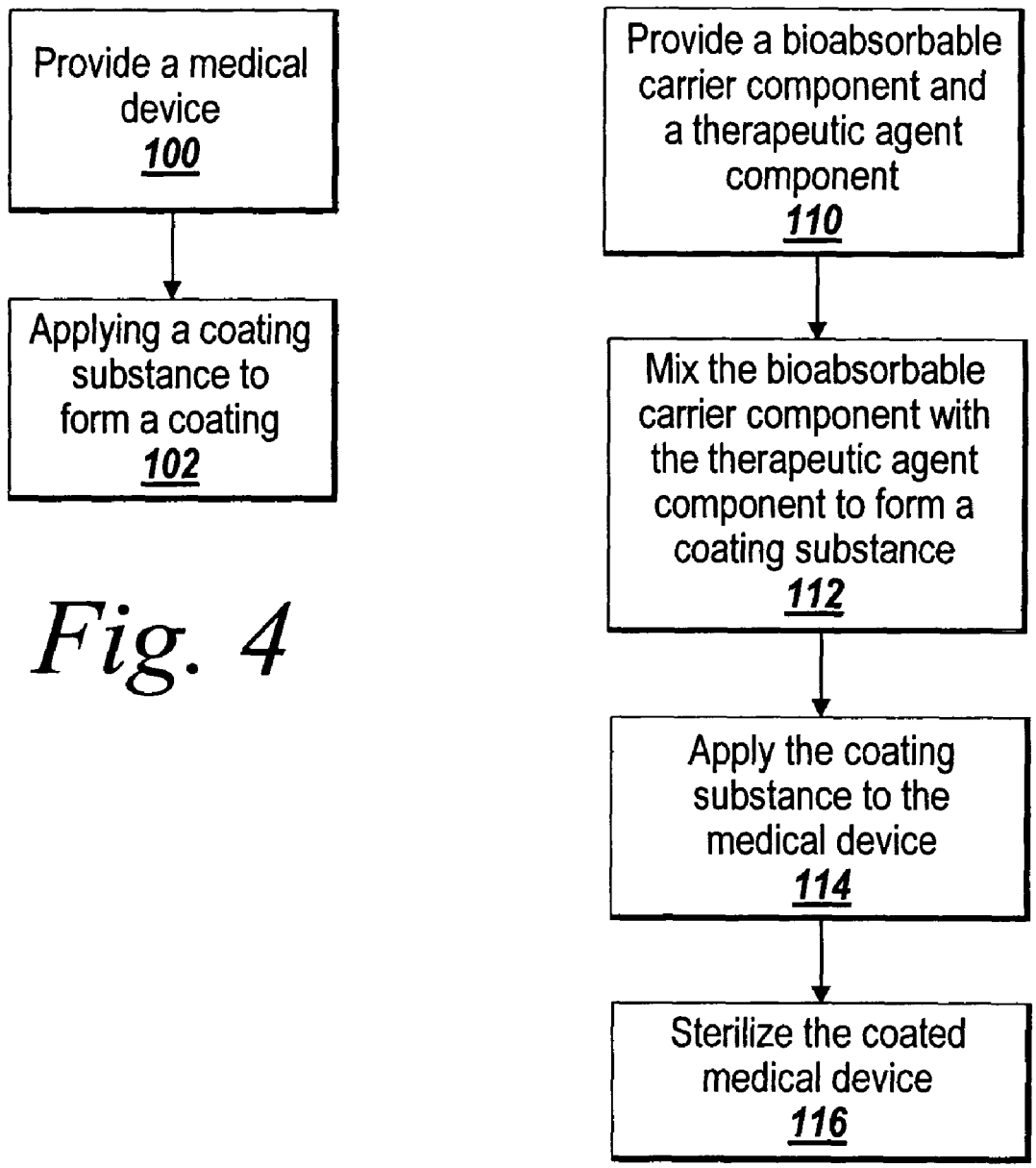
FIG. 4 is a flow chart illustrating a method of making the coated medical device of the present invention, in accordance with one embodiment of the present invention.
FIG. 5 is a flow chart illustrating a variation of the method of FIG. 4, in accordance with one embodiment of the present invention.

FIG. 4 illustrates one method of making the present invention, in the form of the coated stent 10, in accordance with one embodiment of the present invention. The process involves providing a medical device, such as the stent 10 (step 100). A coating, such as coating 20, is then applied to the medical device (step 102). One of ordinary skill in the art will appreciate that this basic method of application of a coating to a medical device such as the stent 10 can have a number of different variations falling within the process described. Depending on the particular application, the stent 10 with the coating 20 applied thereon can be implanted after the coating 20 is applied, or additional steps such as curing, sterilization, and removal of solvent can be applied to further prepare the stent 10 and coating 20. Furthermore, if the coating 20 includes a therapeutic agent that requires some form of activation (such as UV light), such actions can be implemented accordingly.

Furthermore, the step of applying a coating substance to form a coating on the medical device such as the stent 10 can include a number of different application methods. For example, the stent 10 can be dipped into a liquid solution of the coating substance. The coating substance can be sprayed onto the stent 10, which results in application of the coating substance on the exterior surface 18 of the stent 10 as shown in FIG. 3. Another alternative application method is painting the coating substance on to the stent 10, which also results in the coating substance forming the coating 20 on the exterior surface 18 as shown in FIG. 3. One of ordinary skill in the art will appreciate that other methods, such as electrostatic adhesion and other application methods, can be utilized to apply the coating substance to the medical device such as the stent 10. Some application methods may be particular to the coating substance and/or to the structure of the medical device receiving the coating. Accordingly, the present invention is not limited to the specific embodiment described herein, but is intended to apply generally to the application of the coating substance to the medical device, taking whatever precautions are necessary to make the resulting coating maintain desired characteristics.

FIG. 5 is a flowchart illustrating one example implementation of the method of FIG. 4. In accordance with the steps illustrated in FIG. 5, a bio-absorbable carrier component is provided along with a therapeutic agent component (step 110). The provision of the bio-absorbable carrier component and the provision of the therapeutic agent component can occur individually, or in combination, and can occur in any order or simultaneously. The bio-absorbable carrier component is mixed with the therapeutic agent component (or vice versa) to form a coating substance (step 112). The coating substance is applied to the medical device, such as the stent 10, to form the coating (step 114). The coated medical device is then sterilized using any number of different sterilization processes (step 116). For example, sterilization can be implemented utilizing ethylene oxide, gamma radiation, E beam, steam, gas plasma, or vaporized hydrogen peroxide. One of ordinary skill in the art will appreciate that other sterilization processes can also be applied, and that those listed herein are merely examples of sterilization processes that result in a sterilization of the coated stent, preferably without having a detrimental effect on the coating 20.

Figure 6:
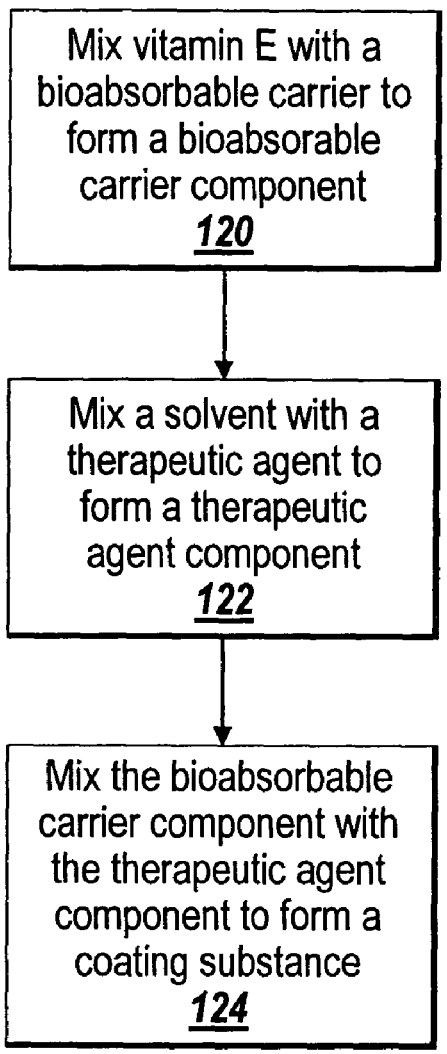
FIG. 6 is a flow chart illustrating another variation of the method of FIG. 4, in accordance with one embodiment of the present invention.
Figure 7:
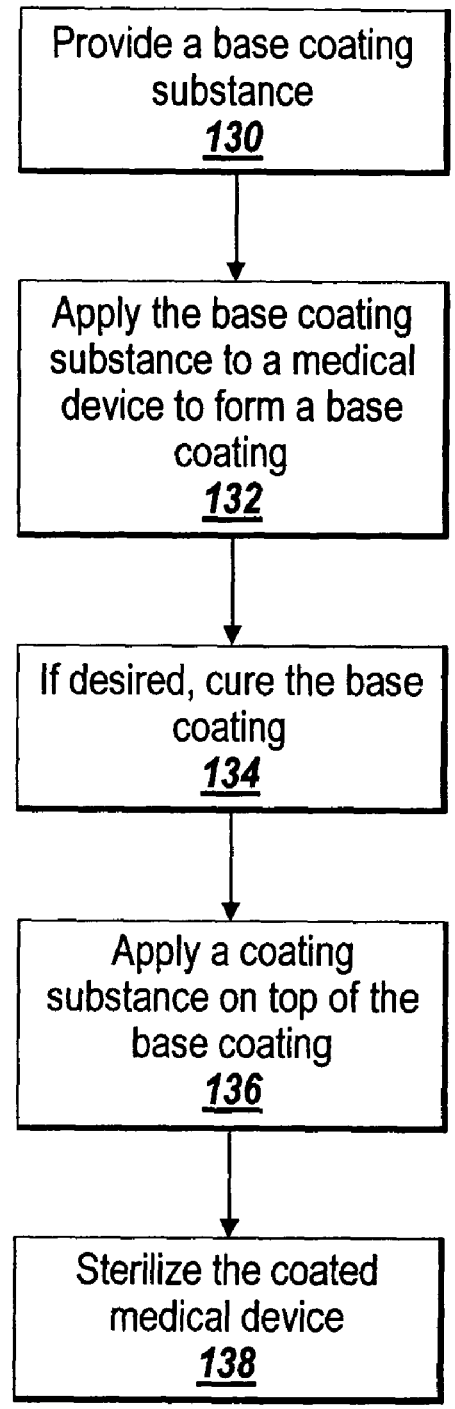
FIG. 7 is a flow chart illustrating another variation of the method of FIG. 4, in accordance with one embodiment of the present invention.

The formation of the bio-absorbable carrier component and the therapeutic agent component can be done in accordance with different methods. FIG. 6 is a flow chart illustrating one example method for forming each of the components. Vitamin E is mixed with a bio-absorbable carrier to form a bio-absorbable carrier component (step 120). A solvent is mixed with a therapeutic agent to form a therapeutic agent component (step 122). The solvent can be chosen from a number of different alternatives, including ethanol or N-Methyl-2-Pyrrolidone (NMP). The bio-absorbable carrier component is then mixed with the therapeutic agent component to form the coating substance (step 124). The solvent can then be removed with vacuum or heat. It should be noted that the preparation of the bio-absorbable carrier component and the therapeutic agent component can be done in either order, or substantially simultaneously. Additionally, in an alternative approach, the solvent can be omitted altogether.

Figure 8:
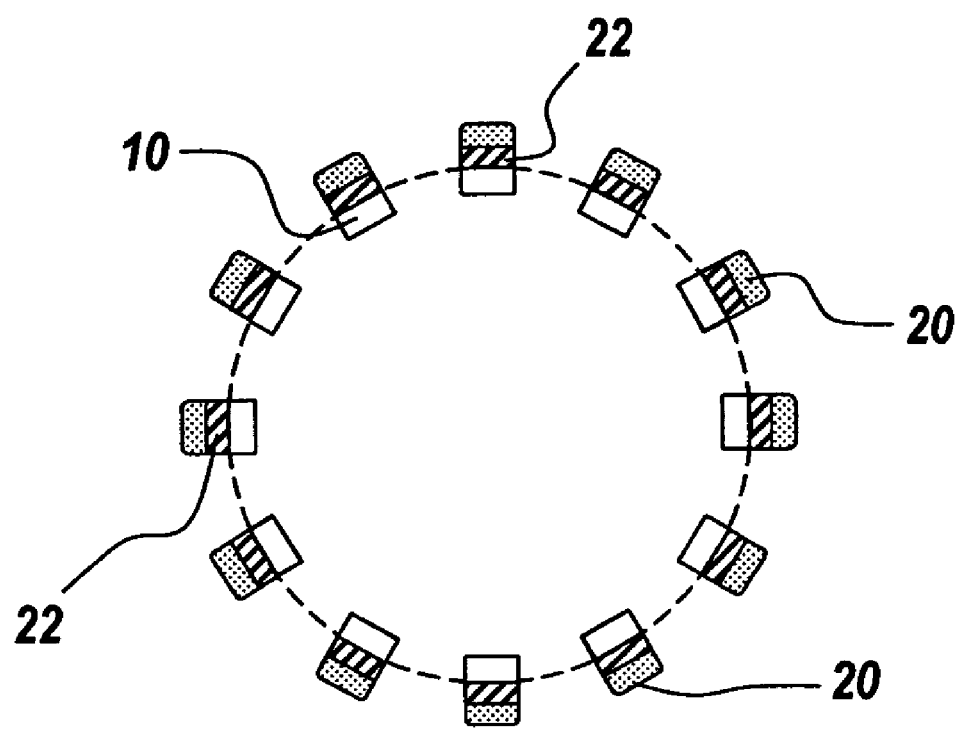
FIG. 8 is a diagrammatic illustration of a coated medical device in accordance with one embodiment of the present invention.

In accordance with another embodiment of the present invention a surface preparation or pre-treatment 22, as shown in FIG. 8, is provided on a stent 10. More specifically and in reference to the flowchart of FIG. 7, a pre-treatment substance is first provided (step 130). The pre-treatment substance is applied to a medical device, such as the stent 10, to prepare the medical device surface for application of the coating (step 132). If desired, the pre-treatment 22 is cured (step 134). Curing methods can include processes such as application of UV light or application of heat to cure the pre-treatment 22. A coating substance is then applied on top of the pre-treatment 22 (step 136). The coated medical device is then sterilized using any number of sterilization processes as previously mentioned (step 138).

FIG. 8 illustrates the stent 10 having two coatings, specifically, the pre-treatment 22 and the coating 20. The pre-treatment 22 serves as a base or primer for the coating 20. The coating 20 conforms and adheres better to the pre-treatment 22 verses directly to the stent 10, especially if the coating 20 is not heat or UV cured. The pre-treatment can be formed of a number of different materials or substances. In accordance with one example embodiment of the present invention, the pre-treatment is formed of a bio-absorbable substance, such as a naturally occurring oil (e.g., fish oil). The bio-absorbable nature of the pre-treatment 22 results in the pre-treatment 22 ultimately being absorbed by the cells of the body tissue after the coating 20 has been absorbed.

It has been previously mentioned that curing of substances such as fish oil can reduce or eliminate some of the therapeutic benefits of the omega-3 fatty acids, including anti-inflammatory properties and healing properties. However, if the coating 20 contains the bio-absorbable carrier component formed of the oil having the therapeutic benefits, the pre-treatment 22 can be cured to better adhere the pre-treatment 22 to the stent 10, without losing all of the therapeutic benefits resident in the pre-treatment 22, or in the subsequently applied coating 20. Furthermore, the cured pre-treatment 22 provides better adhesion for the coating 20 relative to when the coating 20 is applied directly to the stent 10 surface. In addition, the pre-treatment 22, despite being cured, remains bio-absorbable, like the coating 20.

The pre-treatment 22 can be applied to both the interior surface 16 and the exterior surface 18 of the stent 10, if desired, or to one or the other of the interior surface 16 and the exterior surface 18. Furthermore, the pre-treatment 22 can be applied to only portions of the surfaces 16 and 18, or to the entire surface, if desired.

The application of the coating 20 to the stent 10, or other medical device, can take place in a manufacturing-type facility and subsequently shipped and/or stored for later use. Alternatively, the coating 20 can be applied to the stent 10 just prior to implantation in the patient. The process utilized to prepare the stent 10 will vary according to the particular embodiment desired. In the case of the coating 20 being applied in a manufacturing-type facility, the stent 10 is provided with the coating 20 and subsequently sterilized in accordance with any of the methods provided herein, and/or any equivalents. The stent 10 is then packaged in a sterile environment and shipped or stored for later use. When use of the stent 10 is desired, the stent is removed from the packaging and implanted in accordance with its specific design.

In the instance of the coating being applied just prior to implantation, the stent can be prepared in advance. The stent 10, for example, can be sterilized and packaged in a sterile environment for later use. When use of the stent 10 is desired, the stent 10 is removed from the packaging, and the coating substance is applied to result in the coating 20 resident on the stent 10. The coating 20 can result from application of the coating substance by, for example, the dipping, spraying, brushing, swabbing, wiping, printing, or painting methods.

The present invention provides the coating 20 for medical devices such as the stent 10. The coating is bio-absorbable. The coating 20 includes the bio-absorbable carrier component and can include the therapeutic agent component. The coating 20 of the present invention provides a unique vehicle for the delivery of beneficial substances to the body tissue of a patient.

The bio-absorbable carrier component itself, in the form of fish oil for example, can provide therapeutic benefits in the form of reduced inflammation, and improved healing, if the fish oil composition is not substantially modified during the process that takes the naturally occurring fish oil and forms it into the coating 20. Some prior attempts to use natural oils as coatings have involved mixing the oil with a solvent, or curing the oil in a manner that destroys the beneficial aspects of the oil. The solvent utilized in the coating 20 of the exemplar embodiment of the present invention (NMP) does not have such detrimental effects on the therapeutic properties of the fish oil. Thus the omega-3 fatty acids, and the EPA and DHA substances are substantially preserved in the coating of the present invention. Furthermore, the coating 20 of the present invention is not heat cured or UV light cured to an extent that would destroy all or a substantial amount of the therapeutic benefits of the fish oil, unlike some prior art attempts.

Therefore, the coating 20 of the present invention includes the bio-absorbable carrier component in the form of the naturally occurring oil (i.e., fish oil, or any equivalents). The bio-absorbable carrier component is thus able to be absorbed by the cells of the body tissue. More specifically, there is a phospholipid layer in each cell of the body tissue. The fish oil, and equivalent oils, contain lipids as well. There is a lipophilic action that results where the lipids are attracted by each other in an effort to escape the aqueous environment surrounding the lipids. Accordingly the lipids attract, the fish oil fatty acids bind to the cells of the tissue, and subsequently alter cell membrane fluidity and cellular uptake. If there is a therapeutic agent component mixed with the bio-absorbable carrier component, the therapeutic component associated with the fish oil lipids penetrates the cells in an altered manner.

As previously mentioned, prior attempts to create drug delivery platforms such as coatings on stents primarily make use of polymer based coatings to provide the ability to better control the release of the therapeutic agent. Essentially, the polymer in the coating releases the drug or agent at a predetermined rate once implanted at a location within the patient. Regardless of how much of the therapeutic agent would be most beneficial-to the damaged tissue, the polymer releases the therapeutic agent based on properties of the polymer coating. Accordingly, the effect of the coating is substantially local at the surface of the tissue making contact with the coating and the stent. In some instances the effect of the coating is further localized to the specific locations of stent struts pressed against the tissue location being treated. These prior approaches can create the potential for a localized toxic effect.

Contrarily with the present invention, because of the lipophilic mechanism enabled by the bio-absorbable lipid based coating 20 formed using a cross-linked gel derived from at least one fatty acid compound in accordance with the present invention, the uptake of the therapeutic agent is facilitated by the delivery of the therapeutic agent to the cell membrane by the bio-absorbable carrier component. Further, the therapeutic agent is not freely released into the body fluids, but rather, is delivered directly to the cells and tissue. In prior configurations using polymer based coatings, the drugs were released at a rate regardless of the reaction or need for the drug on the part of the cells receiving the drug.

In addition, the bio-absorbable nature of the carrier component and the resulting coating (in the instances where a bio-absorbable therapeutic agent component is utilized) results in the coating 20 being completely absorbed over time by the cells of the body tissue. There is no break down of the coating into sub parts and substances which induce an inflammatory response that are eventually distributed throughout the body and in some instances disposed of by the body, as is the case with biodegradable coatings. The bio-absorbable nature of the coating 20 of the present invention results in the coating being absorbed, leaving only the stent structure, or other medical device structure. There is no foreign body inflammatory response to the bio-absorbable carrier component.

Despite action by the cells, the coating 20 of the present invention is further configured to release the therapeutic agent component at a rate no faster than a selected controlled release rate over a period of weeks to months. The controlled release rate action is achieved by providing an increased level of vitamin E in the mixture with the fish oil, to create a more viscous, sticky, coating substance that better adheres and lasts for a longer duration on the implanted medical device. The controlled release rate can include an initial burst of release, followed by the sustained multi-week to multi-month period of release. Correspondingly, with a greater amount of fatty acids relative to the level of vitamin E, the controlled release rate can be increased. The fatty acids can be found in the oil, and/or fatty acids such as myristic acid can be added to the oil. Thus, the ratio of fatty acids to alpha-tocopherol can be varied in the preparation of the coating 20 to vary the subsequent release rate of the therapeutic agent in a controlled and predictable manner.

In addition, the oil provides a lubricious surface against the vessel walls. As the stent 10 having the coating 20 applied thereon is implanted within a blood vessel, for example, there can be some friction between the stent walls and the vessel walls. This can be injurious to the vessel walls, and increase injury at the diseased vessel location. The use of the naturally occurring oil, such as fish oil, provides extra lubrication to the surface of the stent 10, which reduces the initial injury. With less injury caused by the stent, there is less of an inflammatory response, and less healing required.

Several example implementations have been carried out to demonstrate the effectiveness of the coating 20 of the present invention. Details concerning the example implementations follow.

EXAMPLE #1

A bio-absorbable carrier component was made by mixing 70% vitamin E and 30% EPAX 3000 TG Fish Oil. Cilostazol was mixed with NMP at a loading of 2.5% by weight to form a therapeutic agent component. The bio-absorbable carrier component was mixed at a ratio of 1:1 with the therapeutic agent component to form a coating substance. The coating substance was applied to a stent and dried in a vacuum chamber for 15 minutes. The stent with the coating was then placed in phosphate buffered saline (PBS) for dissolution to measure the delivery of the Cilostazol drug.

EXAMPLE #2

A bio-absorbable carrier component was made by mixing 30% vitamin E and 70% EPAX 3000 TG Fish Oil. Cilostazol was mixed with NMP at a loading of 2.5% by weight to form a therapeutic agent component. The bio-absorbable carrier component was mixed at a ratio of 1:1 with the therapeutic agent component to form a coating substance. The coating substance was applied to a stent and dried in a vacuum chamber for 15 minutes. The stent with the coating was then placed in phosphate buffered saline (PBS) for dissolution to measure the delivery of the Cilostazol drug.

EXAMPLE #3

A bio-absorbable carrier component was made by mixing 30% vitamin E and 70% EPAX 3000 TG Fish Oil. Cilostazol was mixed with NMP at a loading of 2.5% by weight to form a therapeutic agent component. The bio-absorbable carrier component was mixed at a ratio of 1:1 with the therapeutic agent component to form a coating substance. The coating substance was applied to a stent and dried in a vacuum chamber for 15 minutes. The stent was placed in an oven for 5 days at 150° F. The stent with the coating was then placed in phosphate buffered saline (PBS) for dissolution to measure the delivery of the Cilostazol drug.

EXAMPLE #4

A bio-absorbable carrier component was made by mixing 30% vitamin E and 70% EPAX 3000 TG Fish Oil. Cilostazol was mixed with NMP at a loading of 2.5% by weight to form a therapeutic agent component. The bio-absorbable carrier component was mixed at a ratio of 1:1 with the therapeutic agent component to form a coating substance. The coating substance was applied to a stent and dried in a vacuum chamber for 15 minutes. The stent was placed under UV light for 5 days. The stent with the coating was then placed in phosphate buffered saline (PBS) for dissolution to measure the delivery of the Cilostazol drug.

EXAMPLE #5

A bio-absorbable carrier component was made by mixing 30% vitamin E and 70% EPAX 3000 TG Fish Oil. Cilostazol was mixed with NMP at a loading of 2.5% by weight to form a therapeutic agent component. The bio-absorbable carrier component was mixed at a ratio of 1:1 with the therapeutic agent component to form a coating substance. The coating substance was applied to a stent and dried in a vacuum chamber for 15 minutes. The stent was sent for one cycle of EtO sterilization. The stent with the coating was then placed in phosphate buffered saline (PBS) for dissolution to measure the delivery of the Cilostazol drug.

EXAMPLE #6

A bio-absorbable carrier component was made by mixing 30% vitamin E and 70% Lorodan Fish Oil Fatty Acids. Cilostazol was mixed with NMP at a loading of 2.5% by weight to form a therapeutic agent component. The bio-absorbable carrier component was mixed at a ratio of 1:1 with the therapeutic agent component to form a coating substance. The coating substance was applied to a stent and dried in a vacuum chamber for 15 minutes. The stent with the coating was then placed in phosphate buffered saline (PBS) for dissolution to measure the delivery of the Cilostazol drug.

EXAMPLE #7

A bio-absorbable carrier component was made by mixing 30% vitamin E and 70% Lorodan Fish Oil Fatty Acids. Cilostazol was mixed with NMP at a loading of 2.5% by weight to form a therapeutic agent component. The bio-absorbable carrier component was mixed at a ratio of 1:1 with the therapeutic agent component to form a coating substance. The coating substance was applied to a stent and dried in a vacuum chamber for 15 minutes. The stent was placed in an oven for 5 days at 150° F. The stent with the coating was then placed in phosphate buffered saline (PBS) for dissolution to measure the delivery of the Cilostazol drug.

EXAMPLE #8

A bio-absorbable carrier component was made by mixing 15% vitamin E, 35% EPAX 3000 TG Fish Oil, and 50% Myristic Acid. Cilostazol was mixed with NMP at a loading of 2.5% by weight to form a therapeutic agent component. The bio-absorbable carrier component was mixed at a ratio of 1:1 with the therapeutic agent component to form a coating substance. The coating substance was applied to a stent and dried in a vacuum chamber for 15 minutes. The stent with the coating was then placed in phosphate buffered saline (PBS) for dissolution to measure the delivery of the Cilostazol drug.

EXAMPLE #9

A bio-absorbable carrier component was made by mixing 30% vitamin E, 66.5% EPAX 3000 TG Fish Oil, and 3.5% Linseed Oil. Cilostazol was mixed with NMP at a loading of 2.5% by weight to form a therapeutic agent component. The bio-absorbable carrier component was mixed at a ratio of 1:1 with the therapeutic agent component to form a coating substance. The coating substance was applied to a stent and dried in a vacuum chamber for 15 minutes. The stent was placed in an oven for 5 days at 150° F. The stent with the coating was then placed in phosphate buffered saline (PBS) for dissolution to measure the delivery of the Cilostazol drug.

The results of the above different example implementations measured over a time period of 5 days showed a range of release rates of the Cilostazol drug between about 20 to 65 micrograms at about 1 day to about 25 to 85 micrograms at about 5 days. In other example implementations using Rapamycin with similar formulations, Rapamycin was found present in the vessel tissue after 28 days.

In an additional example implementation, a stent was coated with a primer or pre-treatment of fish oil prior to the application of the drug loaded coating. The details are provided below.

EXAMPLE #10

A stainless steel stent was crimped onto a balloon then coated with EPAX 3000 TG Fish Oil that was heated at 250° F. for approximately 72 hours. This heating action increased the viscosity of the oil to honey-like consistency. The stent was then dipped into a solution of fish oil mixed with vitamin E and solvent. The stent was placed under vacuum pressure to remove the solvent. Subsequent analysis demonstrated that 10 out of 10 sampled areas of the stent maintained a detectable (>µm) amount of coating present on the stent, substantially evenly distributed.

EXAMPLE #11

Control Coating

A bio-absorbable carrier component was made by mixing 50% vitamin E and 50% EPAX 3000 TG Fish Oil. The bio-absorbable carrier component was mixed at a weight ratio of 1:1 with 1-methyl-2-pryrrolidone (NMP) to formulate a coating substance [Formulation A]. The stent/balloon section of an Atrium Flyer® coronary stent system was cleaned prior to coating by dipping it into a sodium bicarbonate solution followed by sonication in ultrapure HPLC grade water for five minutes. The wet stent/balloon was removed from the water and dried using flowing hot air for 2 minutes. The cleaned stent/balloon was immersion dip coated in Formulation A, then removed and exposed to flowing hot air for 30 seconds. The entire stent/catheter assembly was then placed in a vacuum chamber for 15 minutes at a pressure of approximately 50 mTorr. The assembly was removed from the vacuum chamber, a protector sheath was placed over the coated stent/balloon section and the entire stent/catheter assembly was returned to its original hoop package insert, then placed in a Tyvek® pouch, sealed and sterilized using Vaporized Hydrogen Peroxide (VHP). After sterilization the packaged assembly was vacuum sealed in a foil pouch.

A representative coated stent was placed in an appropriate dissolution medium as a control sample when determining drug release in the following samples.

EXAMPLE #12

High Dose Rapamycin (~200 ug/Stent)

A bio-absorbable carrier component was made by mixing 50% vitamin E and 50% EPAX 3000 TG Fish Oil. Rapamycin was mixed with 1-Methyl-2-Pyrrolidone (NMP) solvent at a loading of 350 mg/ml to form a therapeutic agent component. The bio-absorbable carrier component was mixed at a weight ratio of 0.5:1 with the therapeutic agent component to formulate a coating substance [Formulation B]. The stent/balloon section of an Atrium Flyer® coronary stent system was cleaned prior to coating by dipping it into a sodium bicarbonate solution followed by sonication in ultrapure HPLC grade water for five minutes. The wet stent/balloon was then removed from the water and dried using flowing hot air for 2 minutes. The cleaned stent/balloon was then immersion dip coated in Formulation B, then removed and exposed to flowing hot air for 30 seconds. The entire stent/catheter assembly was then placed in a vacuum chamber for 15 minutes at a pressure of approximately 50 mTorr. The assembly was removed from the vacuum chamber, a protector sheath was placed over the coated stent/balloon section and the entire stent/catheter assembly was returned to its original hoop package insert, then placed in a Tyvek® pouch, sealed and sterilized using Vaporized Hydrogen Peroxide (VHP). After sterilization the packaged assembly was vacuum sealed in a foil pouch.

The calculated amount of drug on a 3.0×16 mm stent with this formulation was 200 ug. A representative coated stent sample was then placed in Phosphate Buffered saline (PBS) for dissolution to measure the rapamycin release over time.

EXAMPLE #13

Low Dose Rapamycin (~50 ug/Stent)

A bio-absorbable carrier component was made by mixing 50% vitamin E and 50% EPAX 3000 TG Fish Oil. Rapamycin was mixed with 1-Methyl-2-Pyrrolidone (NMP) solvent at a loading of 85 mg/ml to form a therapeutic agent component. The bio-absorbable carrier component was mixed at a weight ratio of 0.84:1 with the therapeutic agent component to formulate a coating substance [Formulation C].

The stent/balloon section of an Atrium Flyer® coronary stent/catheter system was cleaned prior to coating by dipping the stent into a sodium bicarbonate solution followed by sonication in ultrapure HPLC grade water for five minutes. The wet stent/balloon was removed from the water and dried using flowing hot air for 2 minutes. The cleaned stent/balloon was immersion dip coated in Formulation C, and then exposed to flowing hot air for 30 seconds. The entire stent/catheter assembly was then placed in a vacuum chamber for 15 minutes at a pressure of approximately 50 mTorr. The assembly was removed from the vacuum chamber, and a protector sheath was placed over the coated stent/balloon section. The entire stent/catheter assembly was returned to its original hoop package insert, then placed in a Tyvek® pouch, sealed and sterilized using Vaporized Hydrogen Peroxide (VNW). After sterilization the packaged assembly was vacuum sealed in a foil pouch.

The calculated amount of drug on a 3.0×16 mm stent with this formulation was 50 ug. A representative coated stent sample was then placed in Phosphate Buffered saline (PBS) for dissolution to measure rapamycin release over time.

EXAMPLE #14

Preparation and Application of Primer

Primer is prepared by heating or UV treating the oil to increase the viscosity. Primer coated stents were prepared for subsequent drug coating as follows. The stent/balloon section of an Atrium Flyer® coronary stent/catheter system was cleaned prior to primer application by dipping into sodium bicarbonate solution followed by sonication in ultrapure HPLC grade water for five minutes. The stent/balloon was removed from the water and dried using flowing hot air for 2 minutes. EPAX 3000TG fish oil was placed in an oven at 250° F. until the viscosity was of the desired consistency, approximately 30 hours. A thin layer of the primer was applied evenly around the surface of the pre-crimped stent/balloon, using an applicator. The primer coated stent/balloon was subsequently coated with the appropriate formulation, as necessary.

EXAMPLE #15

Hot Cilostazol (~105 ug/Stent)

A bio-absorbable carrier component was made by mixing 70% vitamin E and 30% EPAX 3000 TG fish oil. Separately, 100 mg of Cilostazol was mixed with 0.5 ml of NMP (200 mg/ml concentration). Both the drug-solvent mixture and the bio-absorbable carrier component were heated to 150° F. for approximately 10 minutes. Once both mixtures reached temperature, they were combined at a weight ratio of 1:1, gently mixed, and again heated to 150° F. for approximately 5 minutes, until the mixture equilibrated at 150° F., to formulate a coating substance [Formulation D].

A primer coated Atrium Flyer® stent/balloon was prepared as described in Example #14, and immersion dip coated in Formulation D. The entire stent/catheter assembly was then placed in a vacuum chamber for a period of 4 hours at a pressure of approximately 50 mTorr. The assembly was removed from the vacuum chamber, a protector sheath was placed over the coated stent/balloon section and the entire stent/catheter assembly was returned to its original hoop package insert, then placed in a Tyvek® pouch, sealed and sterilized using Vaporized Hydrogen Peroxide (VHP). After sterilization the packaged assembly was vacuum sealed in a foil pouch.

The calculated amount of drug on a 3.0×16 mm stent with this formulation was 105 ug. A representative coated stent sample was then placed in water for dissolution to measure release of Cilostazol drug over time.

When viewed under 20× magnification it was evident that there were substantially fewer crystals present than there were in a similar formulation that was prepared at room temperature.

EXAMPLE #16

Cilostazol High Solids (~388 ug/Stent)

A bio-absorbable carrier component was made by mixing 30% vitamin E and 70% EPAX 3000 TG Fish Oil. The bio-absorbable carrier component was mixed with cilostazol powder at a drug loading of 36% to formulate a coating substance [Formulation E].

The stent/balloon section of an Atrium Flyer® coronary stent system was sonicated in ultrapure HPLC grade water for five minutes. The stent/balloon was removed from the water and dried using flowing hot air for 2 minutes. The cleaned stent/balloon was then coated with Formulation E using an applicator. A protector sheath was then placed over the coated stent/balloon section and the entire stent/catheter assembly was returned to its original hoop package insert, placed in a Tyvek® pouch, sealed and sterilized using Vaporized Hydrogen Peroxide (VHP). After sterilization the packaged assembly was vacuum sealed in a foil pouch.

The calculated amount of drug on a 3.0×16 mm stent with this formulation was 388 ug. A representative coated stent sample was then placed in water for dissolution to measure release of the Cilostazol drug over time.

EXAMPLE #17

Methylprednisolone High Solids (~440 ug/Stent)

A bio-absorbable carrier component was made by mixing 30% vitamin E and 70% EPAX 3000 TG Fish Oil. The bio-absorbable carrier component was mixed with methylprednisolone powder at a drug loading of 40% to formulate a coating substance [Formulation F].

The stent/balloon section of an Atrium Flyer® coronary stent system was cleaned prior to coating by sonication in ultrapure HPLC grade water for five minutes. The wet stent/balloon was then removed from the water and dried using flowing hot air for 2 minutes. The cleaned stent/balloon was coated with Formulation F using an applicator. A protector sheath was then placed over the coated stent/balloon section and the entire catheter assembly was returned to its original hoop package insert, placed in a Tyvek® pouch, sealed and sterilized using Vaporized Hydrogen Peroxide (VHP). After sterilization the sample was vacuum sealed in a foil pouch.

Figure 9:
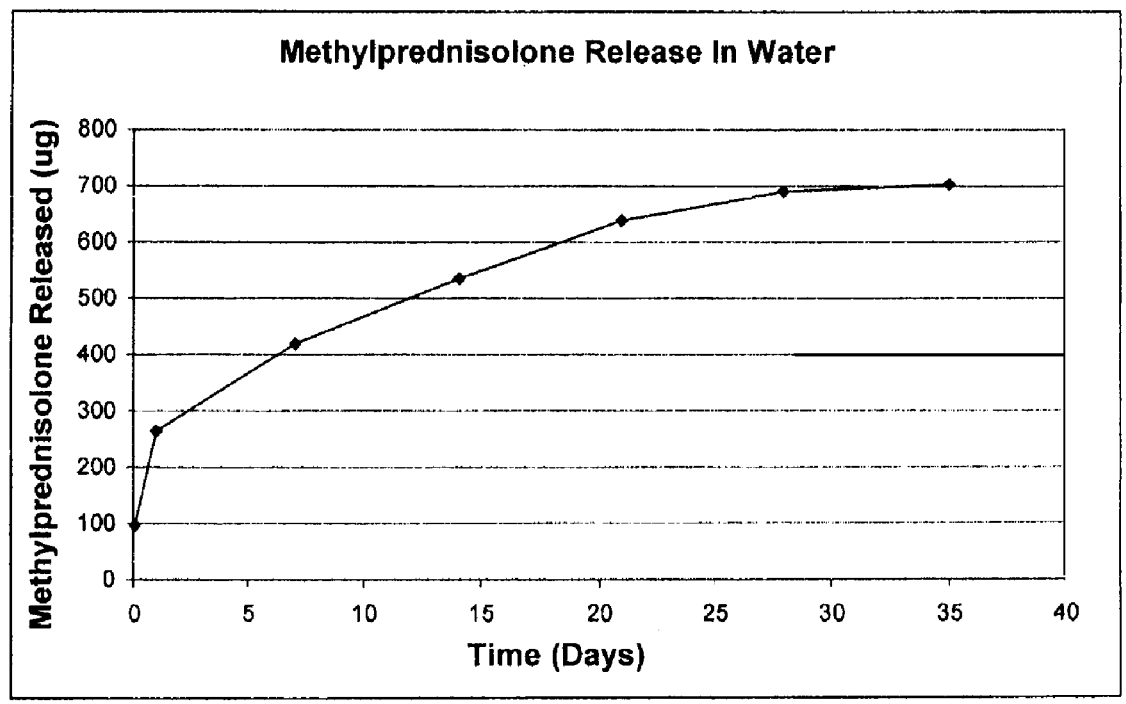
FIG. 9 is a graph depicting the amount of methylprednisone released over time in water from a coated stent prepared in accordance with Example 17.

The calculated amount of drug on a 3.0×16 mm stent with this formulation was approximately 550-700 ug. A representative coated stent sample was then placed in water for dissolution to measure release of the methylprednisolone drug over time. The amount of methylprednisone released over time in water from the coated stent is depicted in FIG. 9.

EXAMPLE #18

High Dose Methylprednisolone

A bio-absorbable carrier component was made by mixing 30% vitamin E and 70% EPAX 3000 TG Fish Oil. Methylprednisolone was mixed with NMP at a loading of 406 mg/ml to form a therapeutic agent component. The bio-absorbable carrier component was mixed at a weight ratio of 0.37:1 with the therapeutic agent component to formulate a coating substance [Formulation G].

The stent/balloon section of an Atrium Flyer® coronary stent system was prepared and primed as described in Example #14. The primer coated stent/balloon was then immersion dip coated in Formulation G. The entire assembly was then placed in a vacuum chamber for 4 hours at a pressure of approximately 50 mTorr. The assembly was removed from the vacuum chamber, a protector sheath was placed over the coated stent/balloon section and the entire assembly was returned to its original hoop package insert, then placed in a sealed Tyvek® pouch and sterilized using Vaporized Hydrogen Peroxide (VHP). After sterilization the sample was vacuum sealed in a foil pouch.

Figure 10:
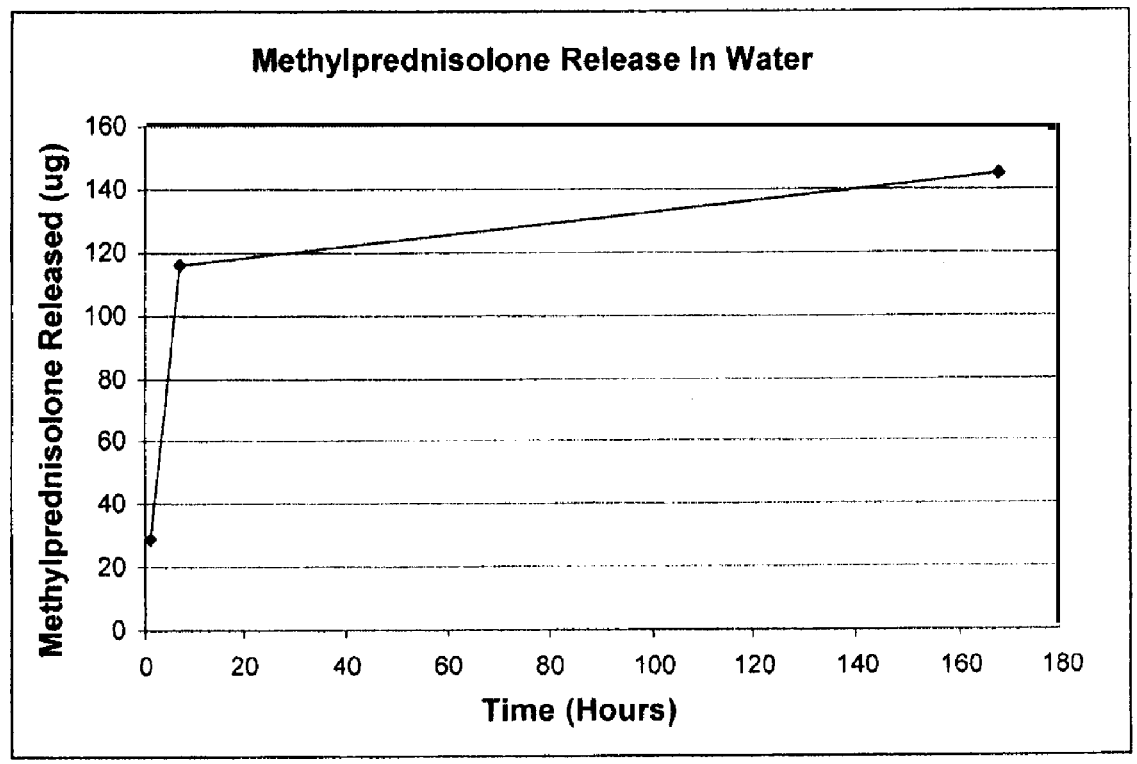
FIG. 10 is a graph depicting the amount of methylprednisone released over time in water from a coated stent prepared in accordance with Example 18.

The calculated amount of drug on a 3.0×16 mm stent with this formulation was 259 ug. A representative coated stent sample was then placed in water for dissolution to measure the release of the methylprednisolone drug over time. The amount of methylprednisone released over time in water from the coated stent is depicted in FIG. 10.

EXAMPLE #19

Low Dose Cilostazol (~30 ug/Stent)

A bio-absorbable carrier component was made by mixing 70% vitamin E and 30% EPAX 3000 TG Fish Oil. Cilostazol was mixed with NMP at a loading of 52 mg/ml to form a therapeutic agent component. The bio-absorbable carrier component was mixed at a weight ratio of 0.9:1 with the therapeutic agent component to formulate a coating substance [Formulation H].

The stent/balloon section of an Atrium Flyer® coronary stent system was prepared and primed as described in Example #14. The primer coated stent/balloon was then immersion dip coated in Formulation H. The entire stent/catheter assembly was then placed in a vacuum chamber for 4 hours at a pressure of approximately 50 mTorr. The assembly was removed from the vacuum chamber, a protector sheath was placed over the coated stent/balloon section and the entire assembly was returned to its original hoop package insert, then placed in a Tyvek® pouch, sealed and sterilized using Vaporized Hydrogen Peroxide (VHP). After sterilization the sample was vacuum sealed in a foil pouch.

Figure 11:
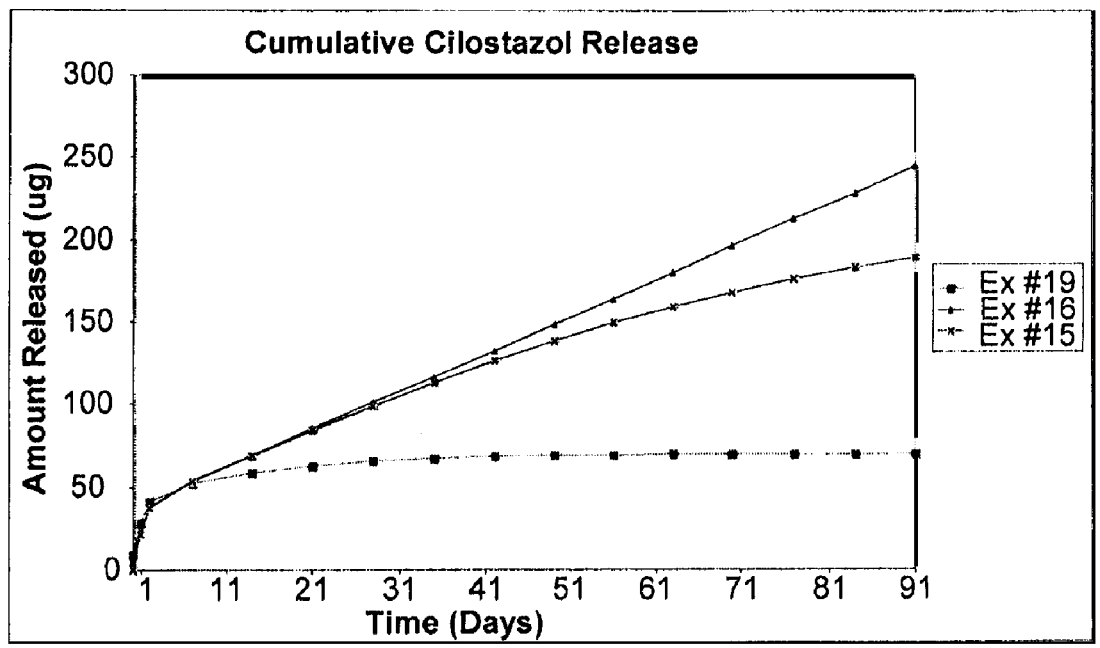
FIG. 11 is a graph depicting the cumulative amount of ciloslazol released over time in water from three individual coated stents prepared in accordance with Examples 15, 16 and 19.

The calculated amount of drug on a 3.0×16 mm stent with this formulation was 30 ug. A representative coated stent sample was then placed in water for dissolution to measure the release of the Cilostazol drug over time. The cumulative amount of cilostazol released over time in water from the coated stent is depicted in FIG. 11.

EXAMPLE #20

Low Dose Methylprednisolone (30 ug/Stent)

A bio-absorbable carrier component was made by mixing 70% vitamin E and 30% EPAX 3000 TG Fish Oil. Methylprednisolone was mixed with NMP at a loading of 56 mg/ml to form a therapeutic agent component. The bio-absorbable carrier component was mixed at a weight ratio of 0.9:1 with the therapeutic agent component to formulate a coating substance [Formulation I].

The stent/balloon section of an Atrium Flyer® coronary stent system was prepared and primed as described in Example #14. The primer coated stent/balloon was then immersion dip coated in Formulation I. The entire stent/catheter assembly was then placed in a vacuum chamber for 4 hours at a pressure of approximately 50 mTorr. The assembly was removed from the vacuum chamber, a protector sheath was placed over the coated stent/balloon section and the entire assembly was returned to its original hoop package insert, then placed in a Tyvek® pouch, sealed-and sterilized using Vaporized Hydrogen Peroxide (VHP). After sterilization the sample was vacuum sealed in a foil pouch.

The calculated amount of drug on a 3.0×16 mm stent with this formulation was 30 ug. A representative coated stent sample was then placed in water for dissolution to measure release of the methylprednisolone drug over time.

EXAMPLE #21

Paclitaxel High Solids (106 ug/Stent)

A bio-absorbable carrier component was made by mixing 30% vitamin E and 70% EPAX 3000 TG Fish Oil. The bio-absorbable carrier component was mixed with paclitaxel powder at a drug loading of 11% to formulate a coating substance [Formulation J].

The stent/balloon section of an Atrium Flyer® coronary stent system was cleaned prior to coating by sonication in ultrapure HPLC grade water for five minutes. The wet stent/balloon was then removed from the water and dried using flowing hot air for 2 minutes. The cleaned stent/balloon was then coated with Formulation J using an applicator. A protector sheath was then placed over the coated stent/balloon section and the entire assembly was returned to its original hoop package insert, placed in a sealed Tyvek® pouch and sterilized using Vaporized Hydrogen Peroxide (VHP). After sterilization the sample was vacuum sealed in a foil pouch.

Figure 12:
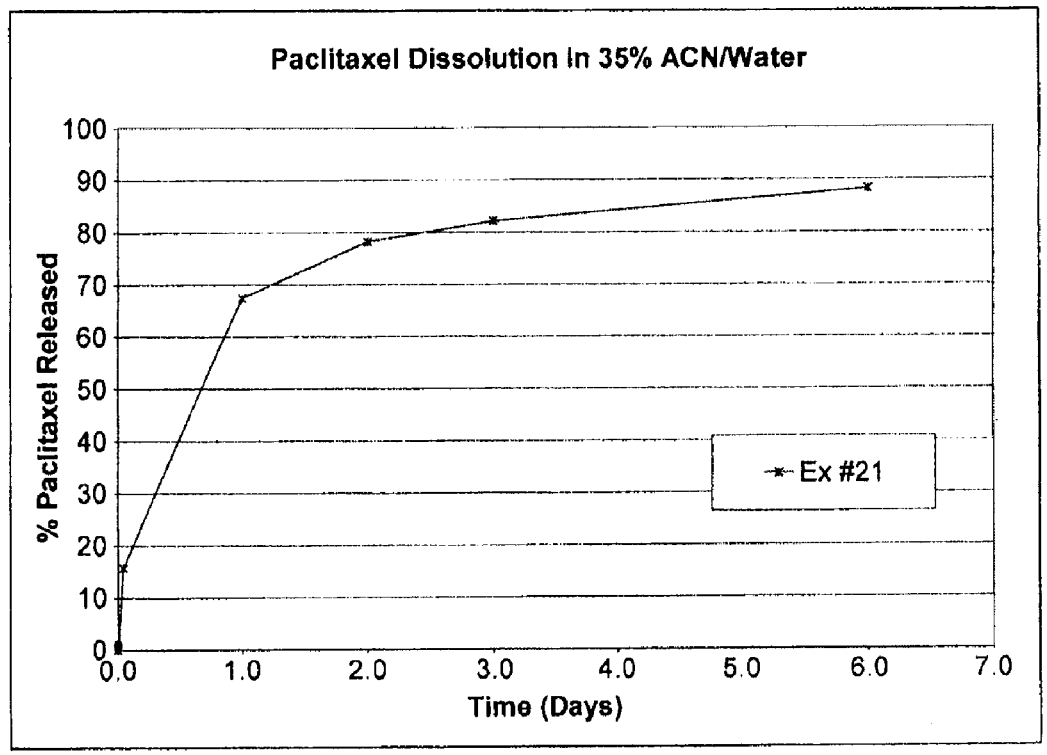
FIG. 12 is a graph depicting the percentage of paclitaxel released over time in a 35% solution of acetonitrile/water from a coated stent prepared in accordance with Example 21.

The calculated amount of drug on a 3.0×16 mm stent with this formulation was 106 ug. A representative coated stent sample was then placed in 35% Acetonitrile/water for dissolution to measure release of the paclitaxel drug over time. The amount of paclitaxel released over time in a 35% solution of acetonitrile/water from the coated stent is depicted in FIG. 12.

EXAMPLE #22

Medium Dose Paclitaxel (30 ug/Stent)

A bio-absorbable carrier component was made by mixing 70% vitamin E and 30% EPAX 3000 TG Fish Oil. Paclitaxel was mixed with Ethanol at a loading of 40 mg/ml to form a therapeutic agent component. The bio-absorbable carrier component was mixed at a weight ratio of 0.94:1 with the therapeutic agent component to formulate a coating substance [Formulation K].

The stent/balloon section of an Atrium Flyer® coronary stent system was prepared and primed as described in Example #14. The primer coated stent/balloon was then immersion dip coated in Formulation K. The entire assembly was then placed in a vacuum chamber for 4 hours at a pressure of approximately 50 mTorr. The assembly was removed from the vacuum chamber, a protector sheath was placed over the coated stent/balloon section and the entire assembly was returned to its original hoop package insert, then placed in a sealed Tyvek® pouch and sterilized using Vaporized Hydrogen Peroxide (VHP). After sterilization the sample was vacuum sealed in a foil pouch.

The calculated amount of drug on a 3.0×16 mm stent with this formulation was 30 ug. A representative coated stent sample was then placed in 35% Acetonitrile/water for dissolution to measure release of the paclitaxel drug over time.

EXAMPLE #23

Low Dose Paclitaxel (5 ug/Stent)

A bio-absorbable carrier component was made by mixing 70% vitamin E and 30% EPAX 3000 TG Fish Oil. Paclitaxel was mixed with Ethanol at a loading of 8 mg/ml to form a therapeutic agent component. The bio-absorbable carrier component was mixed at a weight ratio of 1:1 with the therapeutic agent component to formulate a coating substance [Formulation L].

The stent/balloon section of an Atrium Flyer® coronary stent system was prepared and primed as described in Example #14. The primer coated stent/balloon was then immersion dip coated in Formulation L. The entire assembly was then placed in a vacuum chamber for 4 hours at a pressure of approximately 50 mTorr. The assembly was removed from the vacuum chamber, a protector sheath was placed over the coated stent/balloon section and the entire assembly was returned to its original hoop package insert, then placed in a sealed Tyvek® pouch and sterilized using Vaporized Hydrogen Peroxide (VHP). After sterilization the sample was vacuum sealed in a foil pouch.

The calculated amount of drug on a 3.0×16 mm stent with this formulation was 5 ug. A representative coated stent sample was then placed in 35% Acetonitrile/water for dissolution to measure release of the paclitaxel drug over time.

EXAMPLE #24

High Dose Rapamycin (~200 ug/Stent)

A bio-absorbable carrier component was made by mixing 50% vitamin E and 50% EPAX 3000 TG Fish Oil. Rapamycin was mixed with NMP at a loading of 350 mg/ml to form a therapeutic agent component. The bio-absorbable carrier component was mixed at a weight ratio of 0.5:1 with the therapeutic agent component to formulate a coating substance [Formulation M].

The stent/balloon section of an Atrium Flyer® coronary stent system was cleaned prior to coating by sonication in ultrapure HPLC grade water for five minutes. The wet stent/balloon was then removed from the water and dried using a flowing hot air for 2 minutes. The cleaned stent/balloon was then immersion dip coated in Formulation M then exposed to flowing hot air. The entire assembly was then placed in a vacuum chamber for 4 hours at a pressure of approximately 50 mTorr. The assembly was removed from the vacuum chamber, a protector sleeve was placed over the stent/balloon section and the entire assembly was returned to its original hoop package insert, then placed in a Tyvek® pouch, sealed and sterilized using Vaporized Hydrogen Peroxide (VHP). After sterilization the sample was vacuum sealed in a foil pouch.

The calculated amount of drug on a 3.0×16 mm stent with this formulation was 200 ug. A representative coated stent sample was then placed in Phosphate Buffered saline (PBS) for dissolution to measure release of the rapamycin drug over time.

EXAMPLE #25

Pre-Dried Paclitaxel Formulation

A bio-absorbable carrier component was made by mixing 70% vitamin E and 30% EPAX 3000 TG Fish Oil, as prepared in Example #14. Paclitaxel was mixed with Ethanol at a loading of 39 mg/ml to form a therapeutic agent component. The bio-absorbable carrier component was mixed at a weight ratio of 0.9:1 with the therapeutic agent component to formulate a coating mixture. The coating mixture was then placed in a vacuum chamber at a pressure of approximately 50 mTorr for a period of 16 hours to formulate a coating substance [Formulation N].

The coating substance was highly viscous and free from crystal formation. The stent/balloon section of an Atrium Flyer® coronary stent system was then cleaned prior to coating by sonication in ultrapure HPLC grade water for five minutes. The wet stent/balloon section was then removed from the water and dried using a flowing hot air for 2 minutes. The cleaned stent/balloon was then coated with the Formulation N using an applicator. A protector sheath was then placed over the coated stent/balloon section and the entire assembly was returned to its original hoop package insert, placed in a sealed Tyvek® pouch and sterilized using Vaporized Hydrogen Peroxide (VHP). After sterilization the sample was vacuum sealed in a foil pouch.

The calculated amount of drug on a 3.0×16 mm stent with this formulation was 50 ug. A representative coated stent sample was then placed in 35% acetonitrile/water for dissolution to measure release of the Paclitaxel drug over time.

EXAMPLE #26

Pre Dried Cilostazol Formulation

A bio-absorbable carrier component was made by mixing 70% vitamin E and 30% EPAX 3000 TG Fish Oil, as prepared in Example #14. Cilostazol was mixed with NMP at a loading of 24 mg/ml to form a therapeutic agent component. The bio-absorbable carrier component was mixed at a weight ratio of 0.86:1 with the therapeutic agent component to form a coating mixture. The coating mixture was then placed in a vacuum chamber at a pressure of approximately 50 mTorr for a period of 16 hours to formulate a coating substance [Formulation O].

A highly viscous coating substance that was, free of crystals was obtained. The stent/balloon section of an Atrium Flyer® coronary stent system was then cleaned prior to coating by sonication in ultrapure HPLC grade water for five minutes. The wet stent/balloon section was then removed from the water and dried using flowing hot air for 2 minutes. The cleaned stent/balloon was then coated with Formulation O using an applicator. A protector sheath was then placed over the coated stent/balloon section and the entire assembly was returned to its original hoop package insert, placed in a sealed Tyvek® pouch and sterilized using Vaporized Hydrogen Peroxide (VHP). After sterilization the sample was vacuum sealed in a foil pouch.

A representative coated stent sample was then placed in phosphate buffered saline solution (PBS) for dissolution to measure release of the Cilostazol drug over time.

EXAMPLE #27

Pre Dried Rapamycin Formulation

A bio-absorbable carrier component was made by mixing 70% vitamin E and 30% EPAX 3000 TG Fish Oil. Rapamycin was mixed with NMP at a loading of 97 mg/ml to form a therapeutic agent component. The bio-absorbable carrier component was mixed at a weight ratio of 0.77:1 with the therapeutic agent component to form a coating mixture. The coating mixture was then placed in a vacuum chamber at a pressure of approximately 50 mTorr for a period of 16 hours to formulate a coating substance [Formulation P].

The coating mixture was highly viscous and free from crystal formation. The stent/balloon section of an Atrium Flyer® coronary stent system was then cleaned prior to coating by sonication in ultrapure HPLC grade water for five minutes. The wet stent/balloon section was then removed from the water and dried using flowing hot air for 2 minutes. The cleaned stent/balloon was then coated with the Formulation P using an applicator. A protector sheath was then placed over the coated stent/balloon section and the entire assembly was returned to its original hoop package insert, placed in a sealed Tyvek® pouch and sterilized using Vaporized Hydrogen Peroxide (VHP). After sterilization the sample was vacuum sealed in a foil pouch.

A representative coated stent sample was then placed in phosphate buffered saline solution (PBS) for dissolution to measure release of the Rapamycin drug over time.

EXAMPLE #28

Animal Study

Several different stent and coating combinations were created and implanted into rabbit iliac arteries for 28 days and then histopathology (a measure of biological response to an implant at the cellular level) and histomorphometry (a measure of the neoinitimal thickness and lumen area of the stented vessel) were performed. A bare stent (stent A), a stent having a non-polymer coating of the present invention (stent B), and a stent having a non-polymer coating including a drug (Rapamycin) (stent C) were the three stent and coating combinations using an Atrium Medical Corporation Flyer™ stainless steel stent that were implanted. A polymer coated stent with drug (Rapamycin) made by Johnson & Johnson (Cypher™ stent) (stent D) was a fourth stent combination implanted.

EXAMPLE #29

Release Rate Comparison

Figure 13:
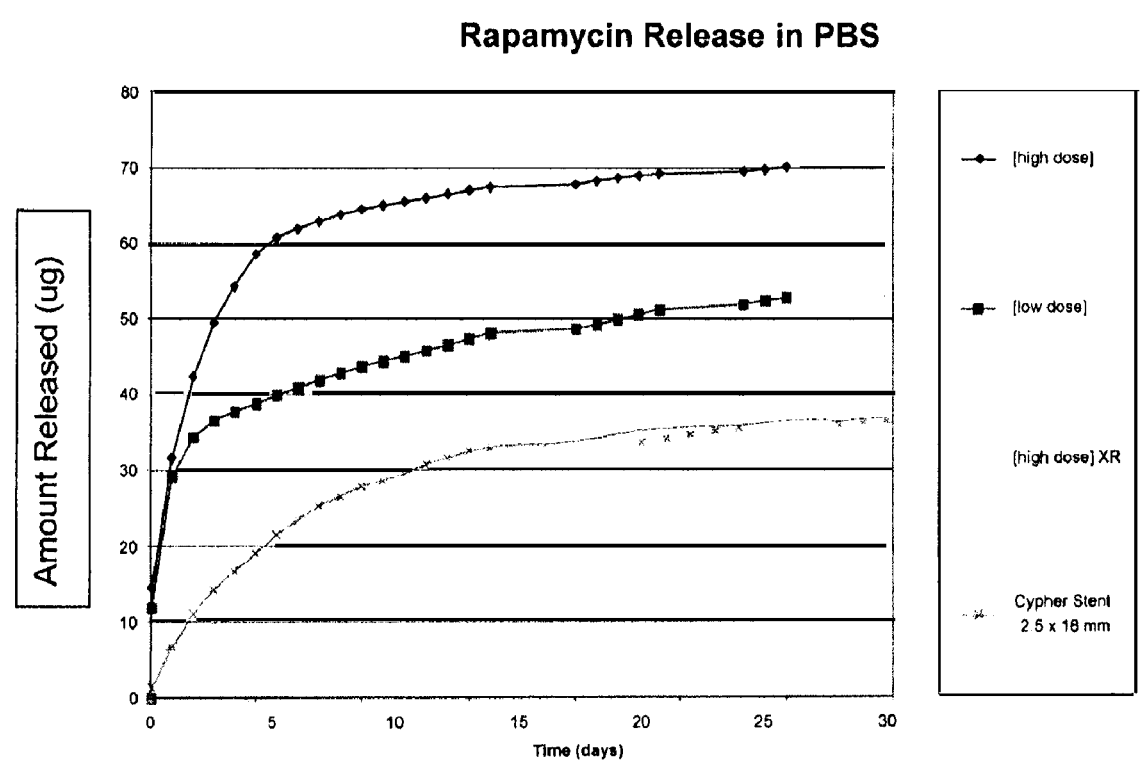
FIG. 13 is a graph comparing the amount of rapamycin released over time in a phosphate buffered saline (PBS) solution from high dose, low dose and high dose extended-release coated stents prepared in accordance with the present invention relative to a CYPHER stent.

Three coatings in accordance with the present invention were applied to the stents having coatings, and the release rates compared. The results are shown in FIG. 13.

Referring to Graph #5, the top diamond line on the curve that is labeled "[high dose]" is a 30.1% Rapamycin formulation made with 50% vitamin E and 50% fish oil. The drug was dissolved in the solvent (NMP) first and then combined with the fish oil/vitamin E mixture and vortexed. The solvent was then removed with vacuum. The formulation was dip coated on stents and then dried over night in a bell jar. The stent was then expanded and submitted for release testing.

The next line on the graph that is labeled "[low dose]" is a sample containing 18.49% rapamycin in a coating that is 30% Vitamin E and 70% fish oil. The coating as made using NMP as the solvent. The solvent was then removed with vacuum. The stent was then expanded and submitted for release testing.

The next line on the graph that is labeled "Cypher stent" was a Cypher stent, measuring 2.5×18 mm. Drug release was measured from an expanded stent.

The final line on the graph that is labeled "[high dose]XR" was a 19.18% Rapamycin insoluble formulation that was made in 30% vitamin E and 70% thickened fish oil. This sample had no solvent and was applied using a stent protector. The sample was then expanded and submitted for release testing.

For purposes of the analysis, the Stents are put into 4 ml vials along with 4 ml of PBS on the incubated (37° C.) shaker table and samples are taken at appropriate time points for measuring drug concentration/release using HPLC. When the stent was ready to be sampled the stent was removed from the vial and put in a new vial with a fresh 4 mls of PBS and returned to the incubated shaker. The sample was prepared for HPLC by adding 600 ul of the PBS from the test sample to 3400 ul of Methanol to obtain an 85:15 ratio. The sample was then mixed using the vortexer. This methanol diluted sample was then injected onto the HPLC and drug release was calculated.

The stents loaded with the bio-absorbable coating of the present invention and low (50 μg) amounts of Rapamycin (labeled [low dose] stent) and the stents loaded with the bio-absorbable coating of the present invention and high (200 μg) amounts of Rapamycin (labeled [high dose] stent) implanted in the iliac arteries were well tolerated and produced no adverse reactions.

The stents having the bio-absorbable coating of the present invention and loaded with Rapamycin significantly reduced neointimal growth, and experienced delayed healing, but the stents were well endothelialized after 28 days. The stents having the bio-absorbable coating of the present invention and the stents having the bio-absorbable coating of the present invention with drug caused relatively less arterial injury relative to the Cypher™ stent (labeled "Cypher stent"), which caused more than twice the amount of arterial injury. The Cypher™ stent produced the greatest reduction in neoinitimal growth, however also had the greatest delay in healing, which was represented by fibrin deposition and poor endothelialization relative to the other implanted stents. The Cypher™ stent also experience relatively greater numbers of inflammatory and giant cells relative to the other implanted stents. The Cypher™ stents experienced at least three times greater amounts of giant cell reaction and the majority of Cypher™ stent struts showed presence of eosinophils, which were rarely present on the other implanted stents.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

What is claimed is:

1. A coated medical device, comprising:
   a coating having cross-linked bio-absorbable carrier component, the bio-absorbable carrier component being at least partially formed of cellular uptake inhibitor and cellular uptake enhancer;
   wherein the cellular uptake enhancer comprises one or more fatty acids selected from the group consisting of eicosapentaenoic acid (EPA), docosahexaenoic acid (DHA) and alpha-linolenic acid (ALA);
   wherein the coating is cured using at least one of heat and ultraviolet light and further includes a therapeutic agent;
   wherein the bioabsorbable carrier component comprises two or more of the fatty acids cross-linked into a substantially random configuration by ester bonds; and controlled delivery of the therapeutic agent to the patient.

2. The device of claim 1, wherein the cellular uptake inhibitor comprises alpha-tocopherol.

3. The device of claim 1, wherein the cellular uptake enhancer further comprises myristic acid.

4. The device of claim 1, wherein the bio-absorbable carrier component comprises at least one component selected from a group of components comprised of a naturally occurring oil, and an oil composition.

5. The device of claim 1, wherein the bio-absorbable carrier component further comprises a fish oil.

6. The device of claim 1, wherein the bio-absorbable carrier component is modified from its naturally occurring state to a state of increased viscosity in the form of a cross-linked gel.

7. The device of claim 6, wherein the modification of the bio-absorbable carrier component from its naturally occurring state to the state of increased viscosity occurs prior to formation of the coating on the device.

8. The device of claim 1, wherein the bio-absorbable carrier component contains omega-3 fatty acids.

9. The device of claim 1, wherein the therapeutic agent component comprises an agent selected from the group consisting of antioxidants, anti-inflammatory agents, anti-coagulant agents, drugs to alter lipid metabolism, anti-proliferatives, anti-neoplastics, anti-fibrotics, immunosuppressive, tissue growth stimulants, functional protein/factor delivery agents, anti-infective agents, imaging agents, anesthetic agents, chemotherapeutic agents, tissue absorption enhancers, anti-adhesion agents, germicides, antiseptics, proteoglycans, GAG's, gene delivery (polynucleotides), analgesics, prodrugs, and polysaccharides (heparin).

10. The device of claim 1, wherein the therapeutic agent component comprises an agent selected from the group consisting of cerivastatin, cilostazol, fluvastatin, lovastatin, paclitaxel, pravastatin, rapamycin, and simvastatin.

11. The device of claim 1, wherein the coating is bio-absorbable.

12. The device of claim 1, wherein the coating inhibits restenosis.

13. The device of claim 1, wherein the coating is prepared by mixing the fatty acids and a solvent.

14. The device of claim 13, wherein the solvent comprises N-Methyl-2-Pyrrolidone (NMP).

15. The device of claim 1, wherein the coating further comprises a compatibilizer and preservative.

16. The device of claim 1, wherein the medical device comprises a stent.

17. The device of claim 16, wherein the stent is formed of a substance selected from the group consisting of stainless steel, Nitinol alloy, nickel alloy, titanium alloy, cobalt-chromium alloy, ceramics, metals, plastics, and polymers.

18. The device of claim 1, wherein the bio-absorbable carrier component is hardened.

19. The device of claim 1, wherein the bio-absorbable carrier component is hardened by mixing the bio-absorbable carrier component with linseed oil.

20. The device of claim 1, further comprising a pre-treatment provided between the medical device and the coating comprising the bio-absorbable carrier component, wherein the pre-treatment improves consistency and conformability and enhances the adhesion of the coating comprising the bio-absorbable carrier component.

21. The device of claim 20, wherein the pre-treatment is bio-absorbable.

22. The device of claim 20, wherein the pre-treatment comprises at least one component selected from a group of components comprised of a naturally occurring oil, and an oil composition.

23. The device of claim 20, wherein the pre-treatment comprises fish oil.

24. The device of claim 20, wherein the pre-treatment is modified from its naturally occurring state to a state of increased viscosity in the form of a cross-linked gel.

25. The device of claim 24, wherein the modification of the pre-treatment from its naturally occurring state to the state of increased viscosity occurs prior to application of the pre-treatment on the device.

26. The device of claim 1, wherein the coating inhibits neointimal growth.

27. The device of claim 1, wherein the coating promotes endothelialization.

28. A coated medical device, comprising:
    a pre-treatment provided on the medical device having a first bio-absorbable carrier component; and
    a coating disposed on top of the pre-treatment, the coating having a cross-linked second bioabsorbable carrier component at least partially formed of cellular uptake inhibitor and cellular uptake enhancer;
    wherein the cellular uptake enhancer comprises one or more fatty acids selected form the group consisting of eicosapentaenoic acid (EPA), docosahexaenoic acid (DHA) and alpha-linolenic acid (ALA);
    wherein the coating is cured using at least one of heat and ultraviolet light and further includes a therapeutic agent;
    wherein the bio-absorbable carrier component comprises two or more of the fatty acids cross-linked into a substantially random configuration by ester bonds;

wherein the pre-treatment improves consistency and conformability and enhances the adhesion of the coating comprising the second bio-absorbable carrier component; and wherein the coated medical device is implantable in a patient to effect controlled delivery of the therapeutic agent to the patient.

29. The device of claim 28, wherein the cellular uptake inhibitors comprise alpha-tocopherol.

30. The device of claim 28, wherein the cellular uptake enhancer further comprises myristic acid.

31. The device of claim 28, wherein the content of the first bio-absorbable carrier component and the second bio-absorbable carrier component is substantially the same.

32. The device of claim 28, wherein one or both of the first and second bio-absorbable carrier components comprises at least one component selected from a group of components comprised of a naturally occurring oil, and an oil composition.

33. The device of claim 28, wherein at least one component of the first and second bio-absorbable carrier components further comprises a fish oil.

34. The device of claim 28, wherein at least one component of the first and second bio-absorbable carrier components is modified from its naturally occurring state to a state of increased viscosity in the form of a cross-linked gel.

35. The device of claim 28, wherein at least one component of the first and second bio-absorbable carrier components contains omega-3 fatty acids.

36. The device of claim 28, wherein the therapeutic agent comprises an agent selected from the group consisting of cerivastatin, cilostazol, fluvastatin, lovastatin, paclitaxel, pravastatin, rapamycin, and simvastatin.

37. The device of claim 28, wherein the coating is bio-absorbable.

38. The device of claim 28, wherein the coating inhibits restenosis.

39. The device of claim 28, wherein the coating is prepared by mixing the fatty acids and a solvent.

40. The device of claim 39, wherein the solvent comprises N-Methyl-2-Pyrrolidone (NMP).

41. The device of claim 28, wherein the coating further comprises a compatibilizer and preservative.

42. The device of claim 28, wherein the medical device comprises a stent.

43. The device of claim 42, wherein the stent is formed of a substance selected from the group consisting of stainless steel, Nitinol alloy, nickel alloy, titanium alloy, cobalt-chromium alloy, ceramics, metals, plastics, and polymers.

44. The device of claim 28, wherein the bio-absorbable carrier component is hardened.

45. The device of claim 28, wherein the bio-absorbable carrier component is hardened by mixing the bio-absorbable carrier component with linseed oil.

46. The device of claim 28, wherein the pre-treatment is bio-absorbable.

47. The device of claim 28, wherein the pre-treatment comprises at least one component selected from a group of components comprised of a naturally occurring oil, and an oil composition.

48. The device of claim 28, wherein the pre-treatment comprises fish oil.

49. The device of claim 28, wherein the pre-treatment is modified from its naturally occurring state to a state of increased viscosity in the form of a cross-linked gel.

50. The device of claim 48, wherein the modification of the pre-treatment from its naturally occurring state to the state of increased viscosity occurs prior to application of the pre-treatment on the device.

51. The device of claim 28, wherein the coating inhibits neointimal growth.

52. The device of claim 28, wherein the coating promotes endothelialization.

53. The device of claim 28, wherein the device is sterilized using at least one method of sterilization selected from a group of methods of sterilization comprising ethylene oxide, gamma radiation, e-beam, steam, gas plasma, and vaporized hydrogen peroxide.

54. The coated medical device of claim 1, wherein the coating is a flexible, solid-like gel structure.

55. The coated medical device of claim 1, wherein the therapeutic agent remains pharmacologically effective after the coating is cured.

56. The coated medical device of claim 1, wherein the coating is cured without the addition of external crosslinking agents.

* * * * *